(12) United States Patent
Omaleki et al.

(10) Patent No.: US 6,500,147 B2
(45) Date of Patent: *Dec. 31, 2002

(54) FLEXIBLE CATHETER

(75) Inventors: Samuel L. Omaleki, Morgan Hill, CA (US); Isaac J. Kim, San Jose, CA (US); Jefferey C. Bleam, Boulder Creek, CA (US); Juan T. Domingo, Union City, CA (US); Andres D. Tomas, Union City, CA (US); Celso J. Bagaoisan, Union City, CA (US)

(73) Assignee: Medtronic PercuSurge, Inc., Santa Rosa, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/253,591

(22) Filed: Feb. 22, 1999

(65) Prior Publication Data

US 2002/0007146 A1 Jan. 17, 2002

(51) Int. Cl.[7] .............................................. A61M 29/00
(52) U.S. Cl. .................. 604/103.09; 604/524; 604/915; 604/96.01; 606/194
(58) Field of Search ............ 604/96.01, 101.01–102.03, 604/103.01, 103.09, 103.11, 524, 912, 915, 919, 164.03; 606/192, 194

(56) References Cited

U.S. PATENT DOCUMENTS

| | | | |
|---|---|---|---|
| 3,467,101 A | | 9/1969 | Fogarty |
| 4,276,874 A | * | 7/1981 | Wolvek et al. ................ 600/18 |
| 4,351,341 A | * | 9/1982 | Goldberg et al. |
| 4,715,378 A | | 12/1987 | Pope, Jr. et al. |
| 4,723,936 A | | 2/1988 | Buchbinder et al. |
| 4,848,344 A | | 7/1989 | Sos et al. |
| RE34,633 E | | 6/1994 | Sos et al. |
| 5,324,259 A | | 6/1994 | Taylor et al. |
| 5,344,402 A | | 9/1994 | Crocker |
| 5,449,343 A | | 9/1995 | Samson et al. |
| 5,456,665 A | | 10/1995 | Postell et al. |
| 5,507,766 A | | 4/1996 | Kugo et al. |
| 5,558,643 A | | 9/1996 | Samson et al. |
| 5,569,200 A | | 10/1996 | Umeno et al. |
| 5,571,089 A | | 11/1996 | Crocker |

(List continued on next page.)

FOREIGN PATENT DOCUMENTS

| | | |
|---|---|---|
| EP | 0 652 026 A1 | 5/1995 |
| EP | 0 550 258 B1 | 7/1996 |
| WO | WO 95/24236 | 9/1995 |
| WO | WO 96/38193 | 5/1996 |
| WO | WO 97/25914 | 7/1997 |

*Primary Examiner*—Anhtuan T. Nguyen
*Assistant Examiner*—Michael M Thompson
(74) *Attorney, Agent, or Firm*—Knobbe Martens Olson & Bear LLP

(57) ABSTRACT

A balloon catheter having improved flexibility in and about its distal end is provided. The flexibility of the catheter is determined in part by improving the properties of a wire or catheter located within the area where the balloon is mounted. In one aspect of the present invention, connecting wires extend through the balloon from the distal end of a catheter body to the proximal end of a core wire. The core wire extends distally away from the connecting wires and the catheter body. In another aspect of the present invention, a core wire is provided having a proximal end extending within the balloon into the catheter tubular body but is not mounted therein. This allows the proximal end of the core wire to "float" within the tubular body, such that when the catheter is advanced through the vasculature of a patient, the core wire may move longitudinally within the tubular body. In another aspect of the present invention, the balloon is mounted over a tubular body which is configured to give the catheter longitudinal flexibility.

24 Claims, 15 Drawing Sheets

U.S. PATENT DOCUMENTS

| | | | |
|---|---|---|---|
| 5,599,326 A | * | 2/1997 | Carter |
| 5,605,162 A | | 2/1997 | Mirzaee et al. |
| 5,605,543 A | | 2/1997 | Swanson |
| 5,649,908 A | | 7/1997 | Itoh |
| 5,695,483 A | | 12/1997 | Samson |
| 5,746,701 A | | 5/1998 | Noone |
| 5,782,809 A | | 7/1998 | Umeno et al. |
| 5,827,231 A | * | 10/1998 | Harada ................ 604/526 |
| 5,908,405 A | | 6/1999 | Imran et al. |
| 5,957,903 A | | 9/1999 | Marzaee et al. |
| 5,993,424 A | | 11/1999 | Lorenzo et al. |

* cited by examiner

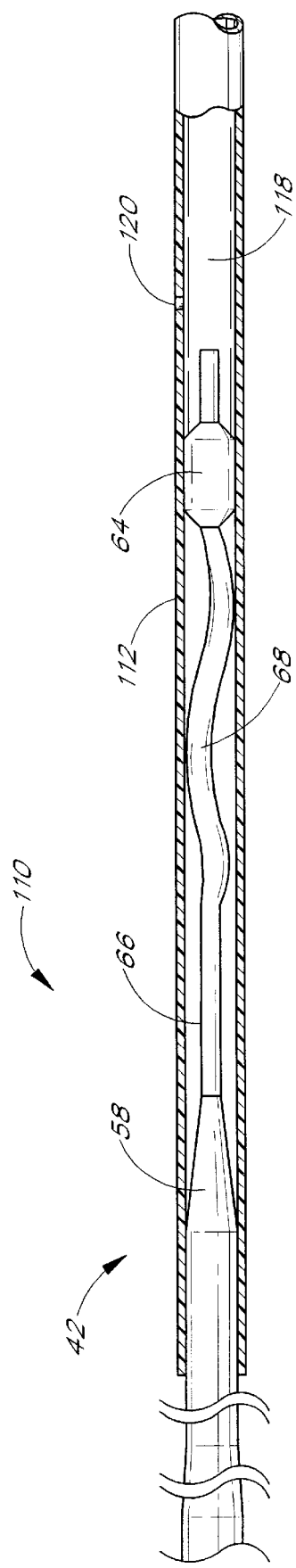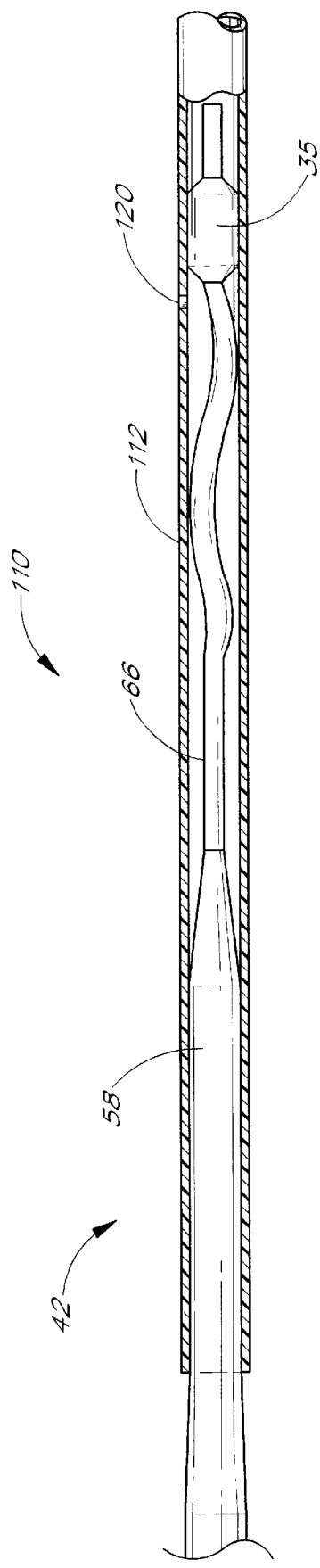

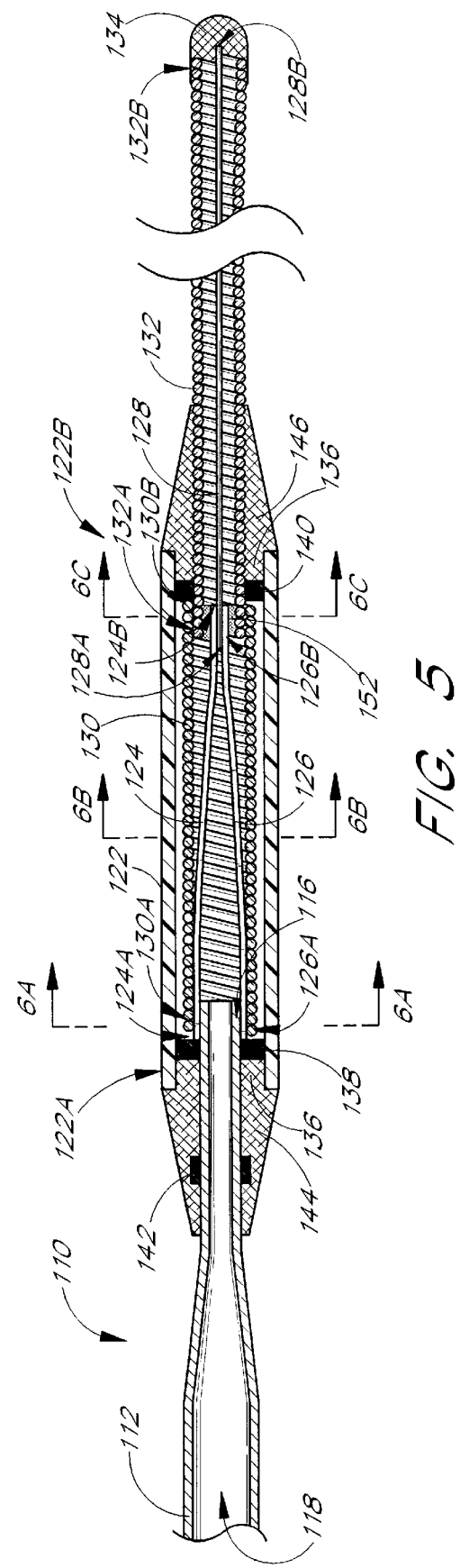

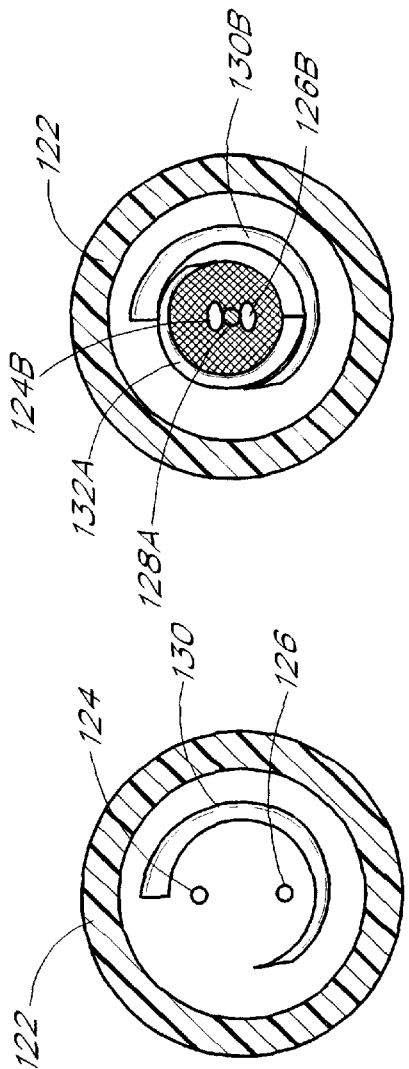
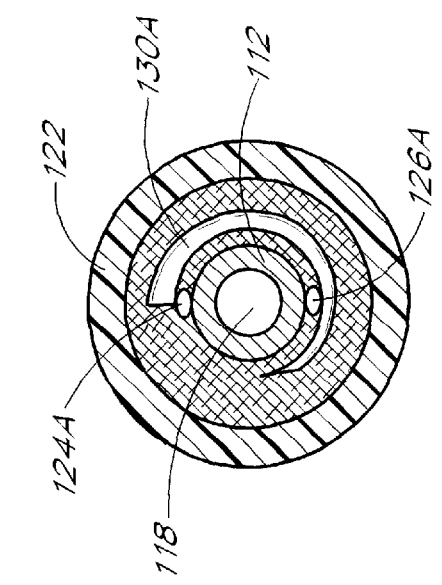
FIG. 6C
FIG. 6B
FIG. 6A

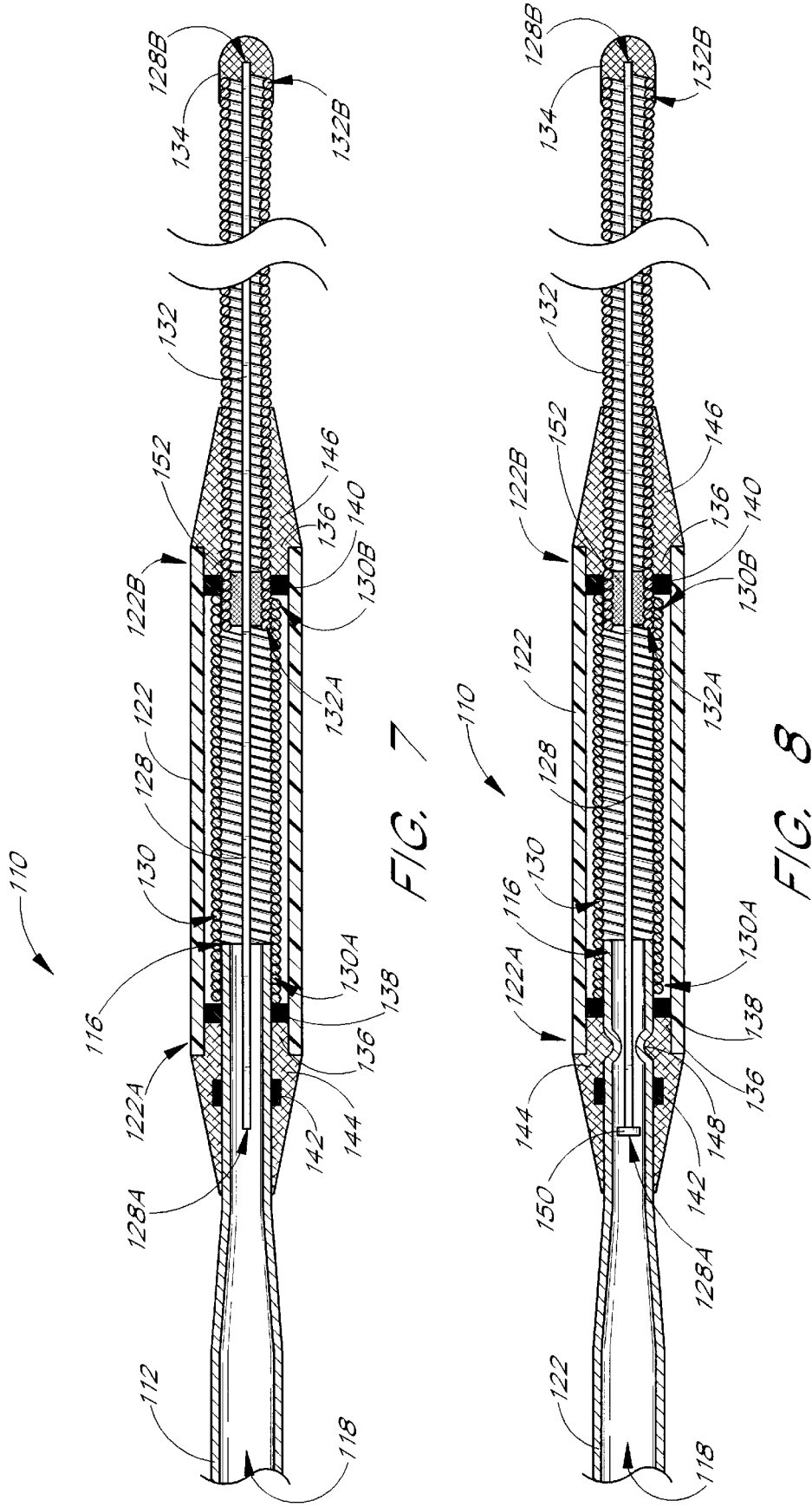

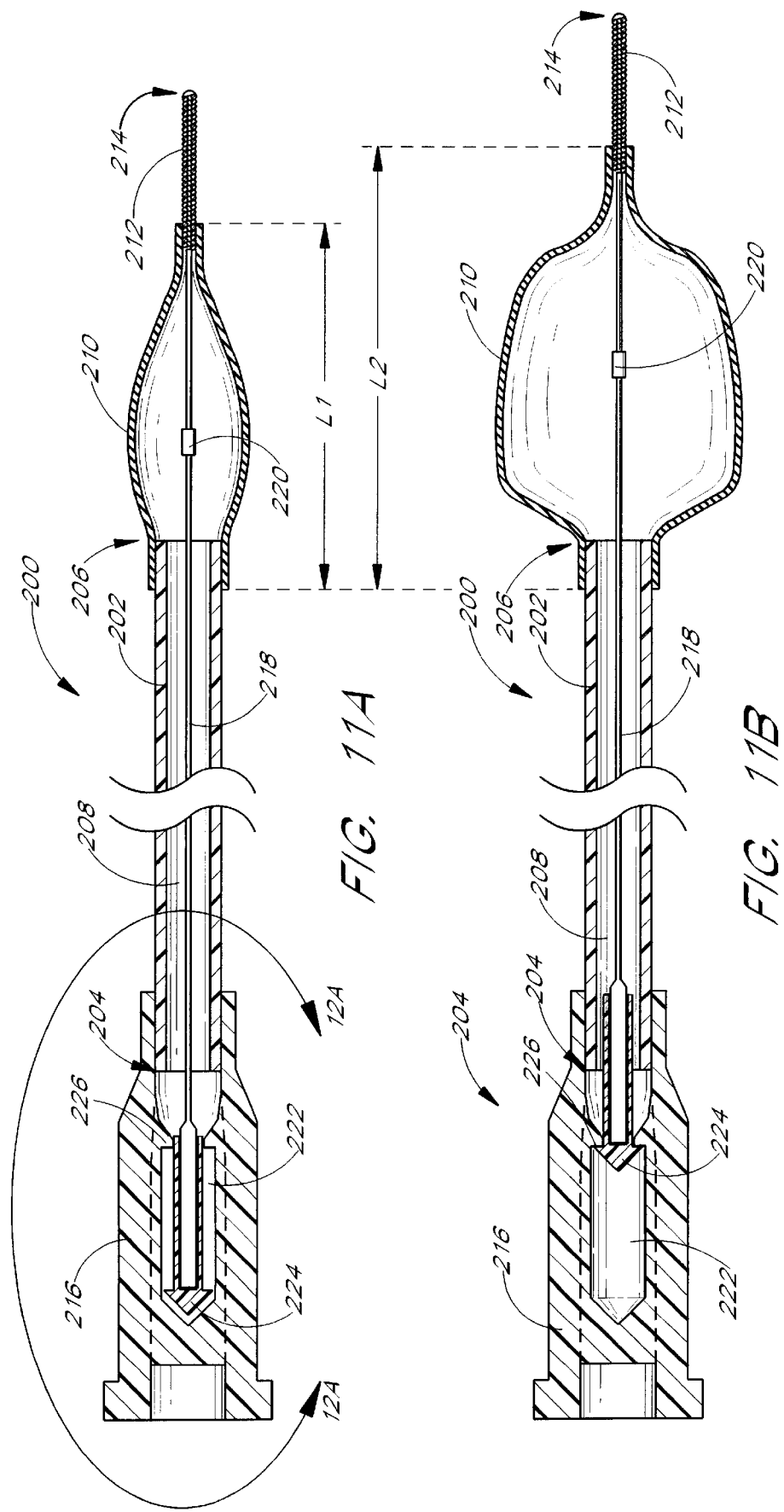

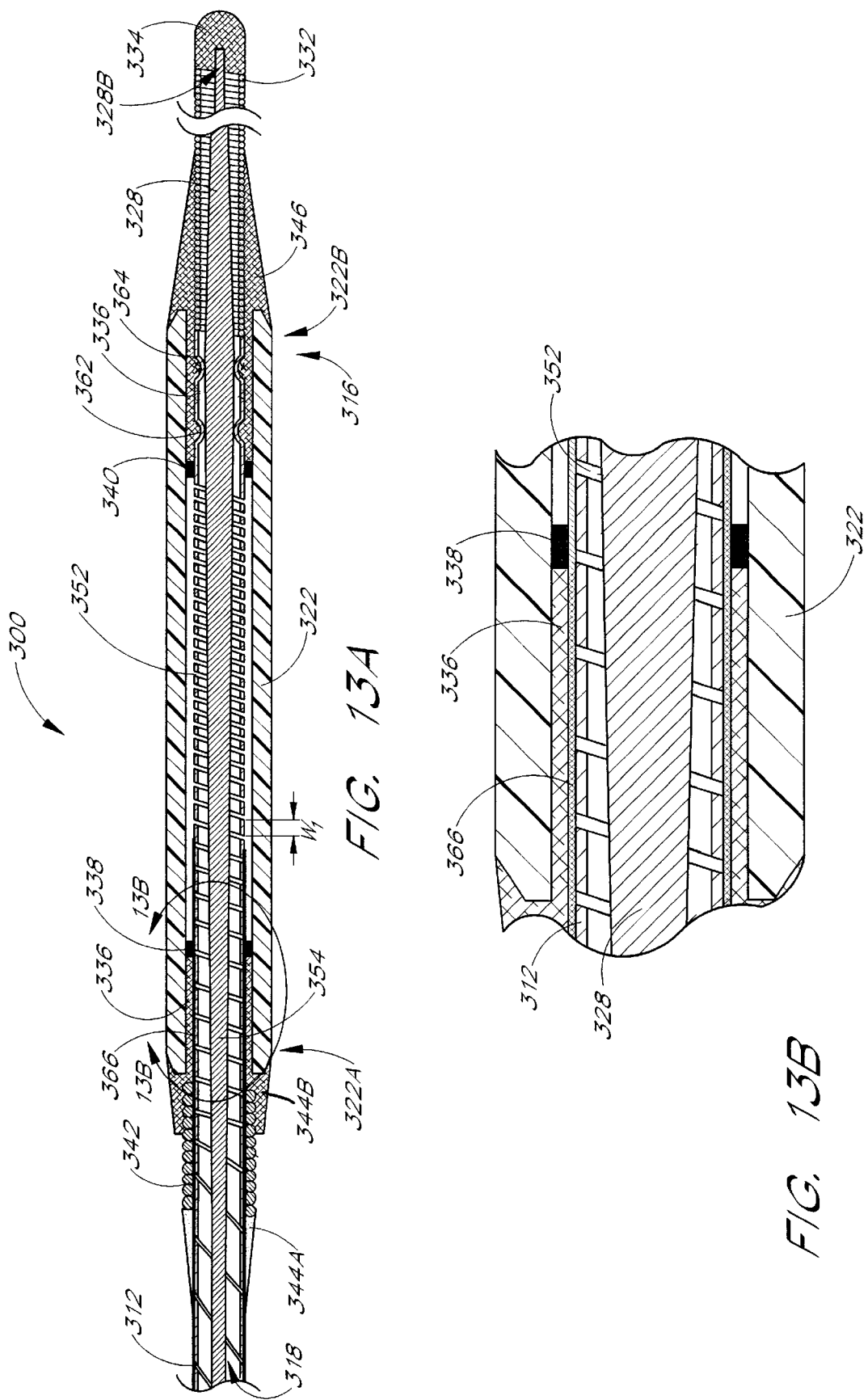

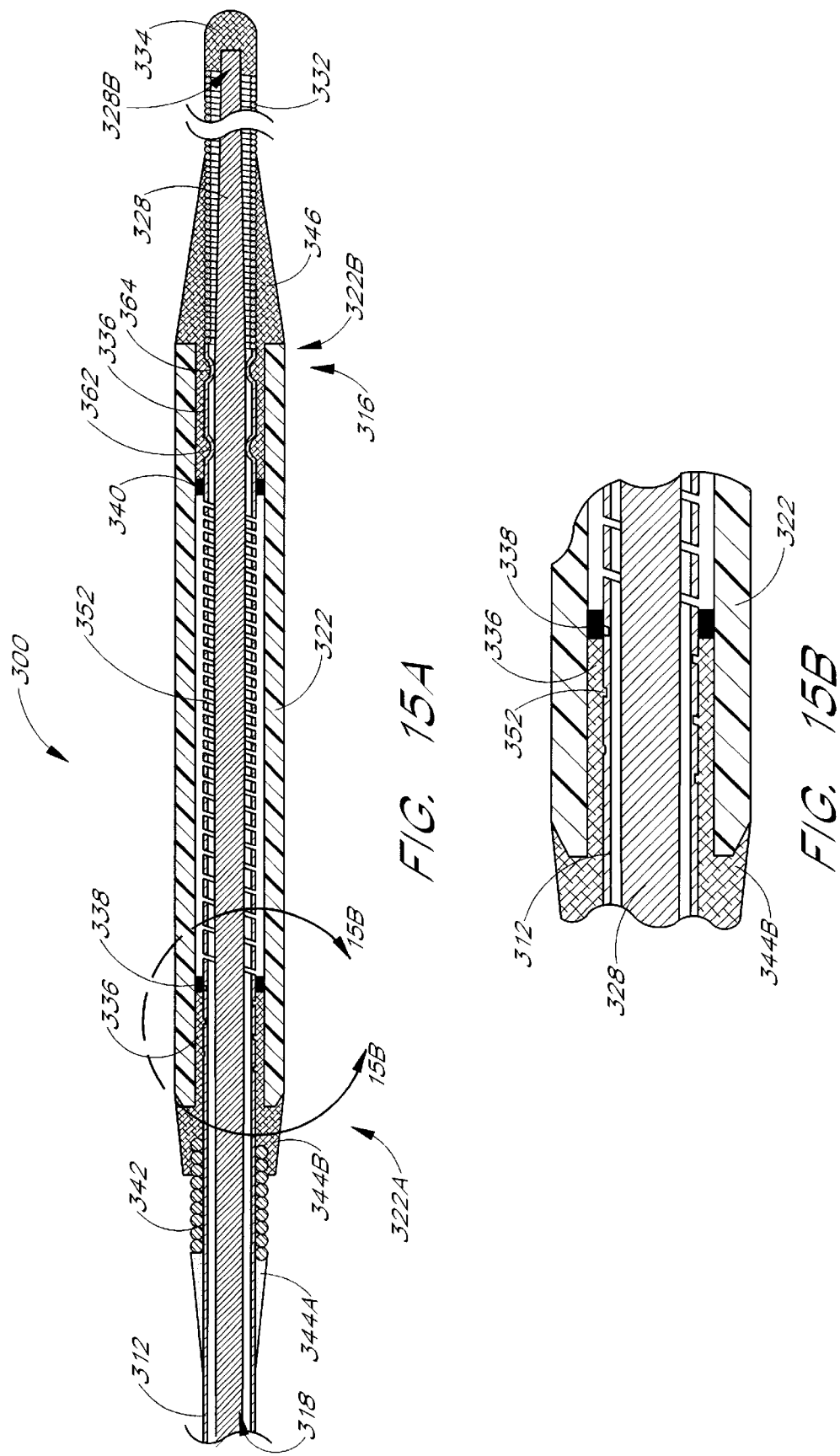

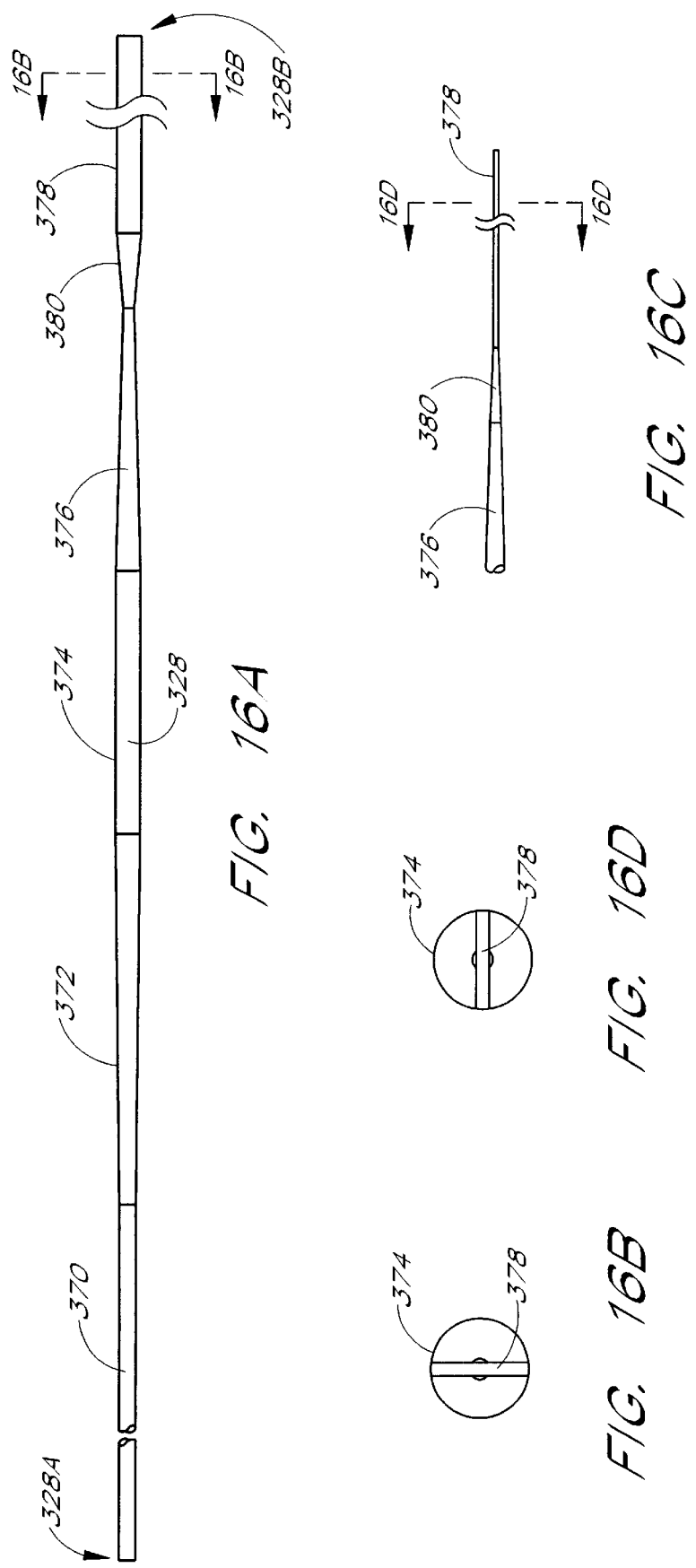

FLEXIBLE CATHETER

BACKGROUND OF THE INVENTION

1. Field of the Invention

This application relates to medical catheters for use in intravascular procedures, and more particularly, to a catheter having improved flexibility at its distal end.

2. Description of the Related Art

Medical catheters such as balloon catheters have been proven efficacious in treating a wide variety of blood vessel disorders. Moreover, these types of catheters have permitted clinicians to treat disorders with minimally invasive procedures that, in the past, would have required complex and perhaps life-threatening surgeries. For example, balloon angioplasty is now a common procedure to alleviate stenotic lesions (i.e., clogged arteries) in blood vessels, thereby reducing the need for heart bypass operations.

Because medical catheters must be passed through a tortuous blood vessel network to reach the intended treatment site, it is desirable that the catheter be fairly flexible, especially at the distal end. However, the distal end must not be so flexible that it tends to bend back upon itself when the clinician advances the catheter distal end through the patient.

One method of imparting desired flexibility characteristics to a catheter has been to incorporate a "core wire" into the distal end of the catheter. A core wire is a wire that extends from the distal end of the catheter body, providing structural support to the distal end to prevent prolapse, bend backs or kinks during catheter advancement. Furthermore, the core wire is also flexible, such that the catheter's distal end may navigate tortuous blood vessel, networks or other body cavities.

However, conventional core wires often do not offer an ideal flexibility profile for the distal end of a catheter. For instance, when a core wire is mounted inside the distal end of a catheter body, because the catheter body is relatively rigid compared to the relatively flexible core wire, an abrupt transition in flexibility is produced between the core wire and the catheter body. This transition is undesirable because when the catheter is advanced through a tortuous pathway, the catheter may experience a sharp bend at the transition point. This makes it difficult for the catheter to navigate the vessel and increases the likelihood of damage to the vessel.

Moreover, a catheter carrying a balloon or other expandable member on its distal end experiences particular problems related to the flexibility profile of the device. For instance, with many balloon catheters, the transition in flexibility between the catheter portion carrying the balloon and the wire extending past the distal end of the balloon is often too abrupt, leading to the problem that when the catheter is advanced through a blood vessel, the flexible wire is capable of navigating blood vessel turns, but the stiffer portion where the balloon is located cannot. This causes stabbing of the balloon into the walls of the vessel during navigation of tight turns.

Problems also arise in these devices with regard to the dimensional range of the balloon. Balloons mounted on the distal end of the catheters have a tendency to expand not only radially but also longitudinally upon inflation. Depending on the balloon material used, the balloon length may expand minimally (e.g., polyethylene terephthalate) or extensively (e.g., latex or C-Flex). For example, an unmounted C-Flex balloon with a length of about 9 mm has been found to expand longitudinally anywhere from 2 to 20 mm upon inflation. Thus, when the catheters and/or core wires to which these balloons are mounted are too rigid, inflation of the balloon may cause bowing of the catheter and/or core wire and other undesired effects.

Furthermore, balloon centering and rupture are also affected by the flexibility profile of the catheter. In particular, when balloon expansion is limited by the rigidity of the catheter and/or core wire, the balloon cannot uniformly expand. This causes an uneven distribution of stresses within the balloon which causes the balloon to become poorly centered. Moreover, the uneven distribution of stresses can create stress concentration points leading to diminished fatigue life and ultimately quicker balloon failure.

Accordingly, what is needed is an improved balloon catheter offering desired flexibility characteristics around and within the balloon to improve balloon range, centering and rupture properties. What is also needed is a catheter having improved flexibility to exhibit a better transition from the proximal end to the distal end of the catheter.

SUMMARY OF THE INVENTION

The present invention solves the needs described above by providing a catheter having an improved flexibility profile in and about its distal end. In particular, for a catheter carrying a balloon on its distal end, the preferred embodiments of the present invention improve the transition and flexibility of the catheter in and around the area where the balloon is mounted. In one aspect of the present invention, a catheter is provided comprising an elongate body having a proximal end and a distal end. At least one connecting wire having a proximal end and a distal end is provided, the proximal end of the wire being mounted to the distal end of the elongate body and the distal end of the wire extending past the distal end of the elongate body. A core wire is provided having a proximal end connected to the distal end of the connecting wire and extending distally therefrom. In one embodiment, because the core wire is not directly attached to the catheter body, a transition region is provided between the catheter body and the core wire to give the catheter a gradually increasing flexibility.

In another aspect of the present invention, a medical device is provided comprising an elongate body having a proximal end and a distal end. An expandable member is mounted to the distal end of the elongate body. A core wire is provided lying along substantially the same longitudinal axis as the elongate body, the core wire having a proximal end and a distal end. The proximal end of the core wire is located within the expandable member and is spaced distally from the distal end of the elongate body. Means are provided for connecting the elongate body to the core wire.

In another aspect of the present invention, a balloon catheter is provided comprising an elongate tubular body having a proximal end and a distal end and a lumen extending therethrough. An inflatable balloon is mounted over the distal end of the tubular body. A core wire lies along substantially the same longitudinal axis as the tubular body, the core wire having a proximal end and a distal end. The proximal end of the core wire is distally spaced from the distal end of the tubular body outside of the lumen. A plurality of connecting wires connects the distal end of the tubular body to the core wire.

In another aspect of the present invention, a catheter is provided comprising an elongate tubular body having a proximal end and a distal end and a lumen extending therethrough. A core wire having a proximal end and a distal end is provided, wherein the proximal end of the core wire extends into the lumen of the tubular body and the distal end extends distally away from the tubular body. A portion of the core wire is positioned coaxially inside the lumen to create an annular space between the core wire and the tubular body. The annular space extends around the core wire over the entire length of that portion of the core wire inside the lumen. An expandable member is provided having a proximal end mounted over the distal end of the tubular body and a distal end mounted over the core wire distal to the tubular body.

This embodiment in effect allows the proximal end to "float" within the tubular body, such that when the catheter is advanced through the vasculature of a patient, the core wire may move longitudinally within the tubular body. This longitudinal movement creates the effect that the catheter is gradually increasing in flexibility between the tubular body and the core wire, because when the distal end of the catheter bends, the core wire moves distally out of the catheter to make the bend more gradual. Furthermore, when a balloon or other expandable device is mounted between the tubular body and the core wire, the longitudinal movement allowed by the floating core wire further accommodates any longitudinal expansion by the balloon or expandable device upon actuation.

In another aspect of the present invention, a catheter is provided comprising an elongate tubular body having a proximal end and a distal end and a lumen extending therethrough. A core wire having a proximal end and a distal end is provided, the proximal end of the core wire extending into the lumen at the distal end but remaining unattached thereto. A flexible member connects the tubular body to the core wire.

In another aspect of the present invention, a catheter is provided comprising an elongate tubular body having a proximal section and a distal section and a lumen extending therethrough. An expandable member is mounted to the distal section. The distal section is configured to axially expand in response to expansion of the expandable member.

In another aspect of the present invention, a catheter is provided comprising an elongate tubular body having a proximal end and a distal end and a lumen extending therethrough. An expandable member is mounted to the distal end of the tubular body. The tubular body has a coiled section that extends at least partially within the expandable member to provide the tubular body with longitudinal flexibility upon actuation of the expandable member.

In another aspect of the present invention, a catheter is provided comprising an elongate body having a proximal end and a distal end. An expandable member is mounted to the distal end. The elongate body receives cuts at least partially proximal to the expandable member.

In another aspect of the present invention, a catheter is provided comprising an elongate assembly having a distal portion. A balloon is mounted on the distal portion of the elongate assembly, the balloon being comprised of a sheet material attached to the elongate assembly at spaced locations such that the sheet material between the spaced locations expands outwardly in response to inflation pressure to inflate the balloon. The elongate assembly is axially expandable between the spaced locations to accommodate changes in the balloon shape as the balloon is inflated, whereby stresses in the balloon are reduced.

In another aspect of the present invention, a method is provided, comprising providing a catheter comprised of an elongate assembly having a balloon thereon. The balloon is inflated in a body lumen. A portion of the elongate assembly is axially elongated within the balloon during inflation of the balloon to reduce stresses on the balloon material.

BRIEF DESCRIPTION OF THE DRAWINGS

FIGS. 4A and 4B show the open and closed low profile catheter valve positions, respectively.

FIG. 5 is a cross-sectional view of one preferred aspect of the distal end of a balloon catheter, more particularly showing a core wire attached to a tubular body through two connecting wires.

FIGS. 6A, 6B and 6C are cross-sectional views of the catheter shown in FIG. 5, along lines 6A—6A, 6B—6B, and 6C—6C, respectively.

FIG. 7 is a cross-sectional view of another preferred aspect of the distal end of a balloon catheter, more particularly showing a floating core wire within the catheter tubular body.

FIG. 8 is a cross-sectional view of an alternate embodiment of the catheter shown in FIG. 7.

FIG. 11A is a cross-sectional view of a catheter carrying an uninflated balloon on its distal end and having a floating core wire extending therethrough.

FIG. 11B is a cross-sectional view of the catheter in FIG. 11A, showing the balloon inflated.

FIG. 13A is a longitudinal cross-sectional view of the distal end of a balloon catheter having a longitudinally flexible hypotube.

FIG. 13B is an enlarged view of the proximal end of the balloon of FIG. 13A.

FIG. 15A is a cross-sectional view of a balloon catheter having a longitudinally flexible hypotube with a variable cut depth.

FIG. 15B is an enlarged view of the proximal end of the balloon of FIG. 15A.

FIGS. 16A–16D are side views of the core wire inserted into the hypotube of FIG. 13A or FIG. 15A.

DETAILED DESCRIPTION OF THE PREFERRED EMBODIMENTS

The preferred embodiments of the present invention depict balloon catheters having improved flexibility especially in and around the area of the balloon. Although the embodiments are depicted and discussed in the context of being part of a simple occlusive device having a single lumen, it should be appreciated that the principles and aspects of these embodiments are applicable to more complex occlusive devices having structures and functionalities not discussed herein. For example, the present inventors contemplate that the embodiments described herein may be used in occlusive devices functioning as anchorable guidewires or filters. In addition, the embodiments are also applicable to catheters having balloons such as latex or silicone, or to catheters used for dilatation balloons made of materials such as polyethylene terephthalate. Moreover, the embodiments may also be adapted to other types of non-balloon catheters, such as irrigation catheters used in drug delivery or radiation therapy, or catheters carrying other types of expandable members, such as filters and meshes. The tip design of the catheter can also be applicable to ordinary guidewires. Thus, the guidewire may be hollow or solid. The manner of adapting the embodiments described herein to these various structures and functionalities will become apparent to those of skill in the art in view of the description which follows.

I. Overview of Occlusion System

A. Occlusion Balloon Guidewire

Figure 1:
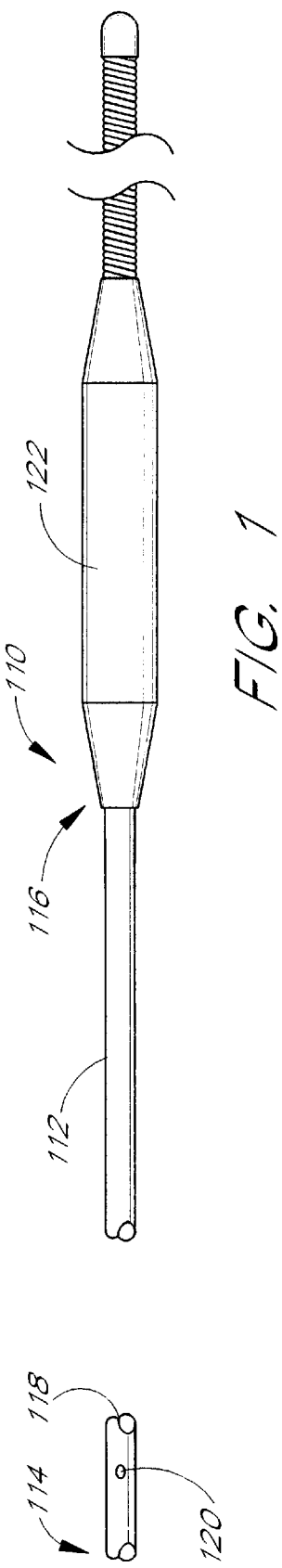
FIG. 1 is a side view of a balloon catheter of the present invention.

The preferred embodiments of the present invention relate to the use an occlusion balloon/guidewire such as generally illustrated in FIG. 1. These guidewires or catheters perform the function of occluding a vessel and allowing for the slidable insertion or advancement of various other catheters and devices. The term "catheter" as used herein is therefore intended to include both guidewires and catheters with these desired characteristics. The term "occlusion" refers to both partial or total occlusion of a vessel.

As shown in FIG. 1, catheter 110 generally comprises an elongate flexible tubular body 112 extending between a proximal control end 114, corresponding to a proximal section of the tubular body 112, and a distal functional end 116, corresponding to a distal section of tubular body 112. Tubular body 112 has a central lumen 118 which extends between ends 114 and 116. An inflation port 120 is provided on tubular body 112 near the proximal end 114. Inflation port 120 is in fluid communication with lumen 118 such that fluid passing through inflation port 120 into or out of lumen 118 may be used to inflate or deflate an inflatable balloon 122 in communication with lumen 118. Inflation port 120 may be similar to existing female luer lock adapters or would be a removable valve at the end. Further details are disclosed in assignee's co-pending application entitled LOW PROFILE CATHETER VALVE AND INFLATION ADAPTER, application Ser. No. 08/975,723, filed Nov. 20, 1997, now U.S. Pat. No. 6,050,972, the entirety of which is hereby incorporated by reference.

The length of tubular body 112 may be varied considerably depending on the desired application. For example, when catheter 110 serves as a guidewire for other catheters in a conventional percutaneous transluminal coronary angioplasty procedure involving femoral artery access, tubular body 112 is comprised of a hollow hypotube having a length in the range from about 160 to about 320 centimeters, with a length of about 180 centimeters being optimal for a single operator device, or 300 centimeters for over the wire applications. Alternatively, for a different treatment procedure not requiring as long a length of tubular body 112, shorter lengths of tubular body 112 may be provided.

Tubular body 112 generally has a circular cross-sectional configuration with an outer diameter within the range from about 0.008 inches to 0.14 inches. In applications where catheter 110 is to be used as a guidewire for other catheters, the outer diameter of tubular body 112 ranges from 0.010 inches to 0.038 inches and preferably is about 0.014 to 0.020 inches in outer diameter or smaller. Noncircular cross-sectional configurations of lumen 118 can also be adapted for use with the catheter 110. For example, triangular, rectangular, oval and other noncircular cross-sectional configurations are also easily incorporated for use with the present invention, as will be appreciated by those of skill in the art. The tubular body 112 may also have variable cross-sections, as described in further detail below.

Tubular body 112 has sufficient structural integrity or "pushability" to permit catheter 110 to be advanced through the vasculature of a patient to distal arterial locations without buckling or undesirable kinking of tubular body 112. It is also desirable for tubular body 112 to have the ability to transmit torque such as in those embodiments where it may be desirable to rotate tubular body 112 after insertion into a patient. A variety of biocompatible materials known by those of skill in the art to possess these properties and to be suitable for catheter manufacture may be used to produce tubular body 112. For example, tubular body 112 may be made of a stainless steel material such as ELGELOY™, or may be made of polymeric material such as PEEK, nylon, polyimide, polyamide, polyethylene or combinations thereof. In one preferred embodiment, the desired properties of structural integrity and torque transmission are achieved by forming tubular body 112 out of an alloy of titanium and nickel, commonly referred to as nitinol. In a more preferred embodiment, the nitinol alloy used to form tubular body 112 is comprised of about 50.8% nickel and the balance titanium, which is sold under the trade name TINEL™ by Memry Corporation. It has been found that a catheter tubular body having this composition of nickel and titanium exhibits an improved combination of flexibility and kink resistance in comparison to other materials. Other details regarding construction of catheter 110 may be found in assignee's copending applications entitled HOLLOW MEDICAL WIRES AND METHODS OF CONSTRUCTING SAME, application Ser. No. 08/812,876, filed Mar. 6, 1997, now U.S. Pat. No. 6,068,623, and SHAFT FOR MEDICAL CATHETERS, application Ser. No. 09/026,105, filed Feb. 19, 1998, now U.S. Patent No. 6,228,072, both of which are hereby incorporated by reference in their entirety.

As illustrated in FIG. 1, an expandable member such as inflatable balloon 122 is mounted on the distal end 116 of tubular body 112. In one preferred embodiment, balloon 122 is a compliant balloon formed of a material comprising a block polymer of styrene-ethylene-butylene-styrene (SEBS), as disclosed in assignee's copending application entitled BALLOON CATHETER AND METHOD OF MANUFACTURE, application Ser. No. 09/026,225, filed on Feb. 19, 1998, the entirety of which is hereby incorporated by reference. Balloon 122 may be secured to tubular body 112 by any means known to those skilled in the art, such as adhesives or heat bonding as described in further detail below. The balloon 122 described in the preferred embodiments has a length of about 5 to 9 mm. Other expandable members are suitable for the catheter 110, such as those disclosed in assignee's copending application entitled OCCLUSION OF A VESSEL, application Ser. No. 09/026,106, filed Feb. 19, 1998, now U.S. Patent No. 6,312,407, the entirety of which is hereby incorporated by reference.

B. Overview of Balloon Inflation/Deflation

Figure 2:
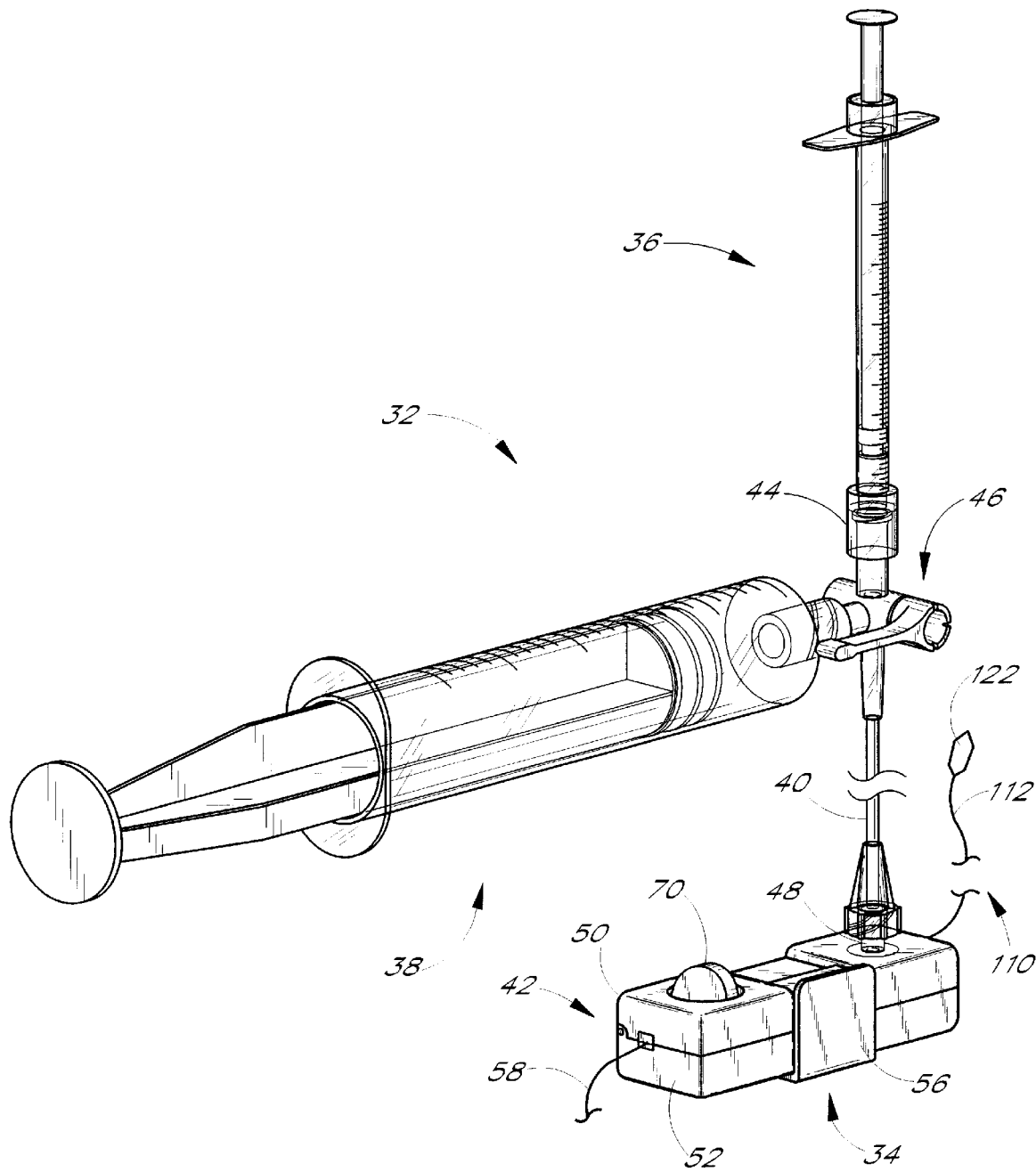
FIG. 2 illustrates a syringe assembly operably coupled to an inflation adapter at a proximal portion of a balloon catheter.
Figure 3:
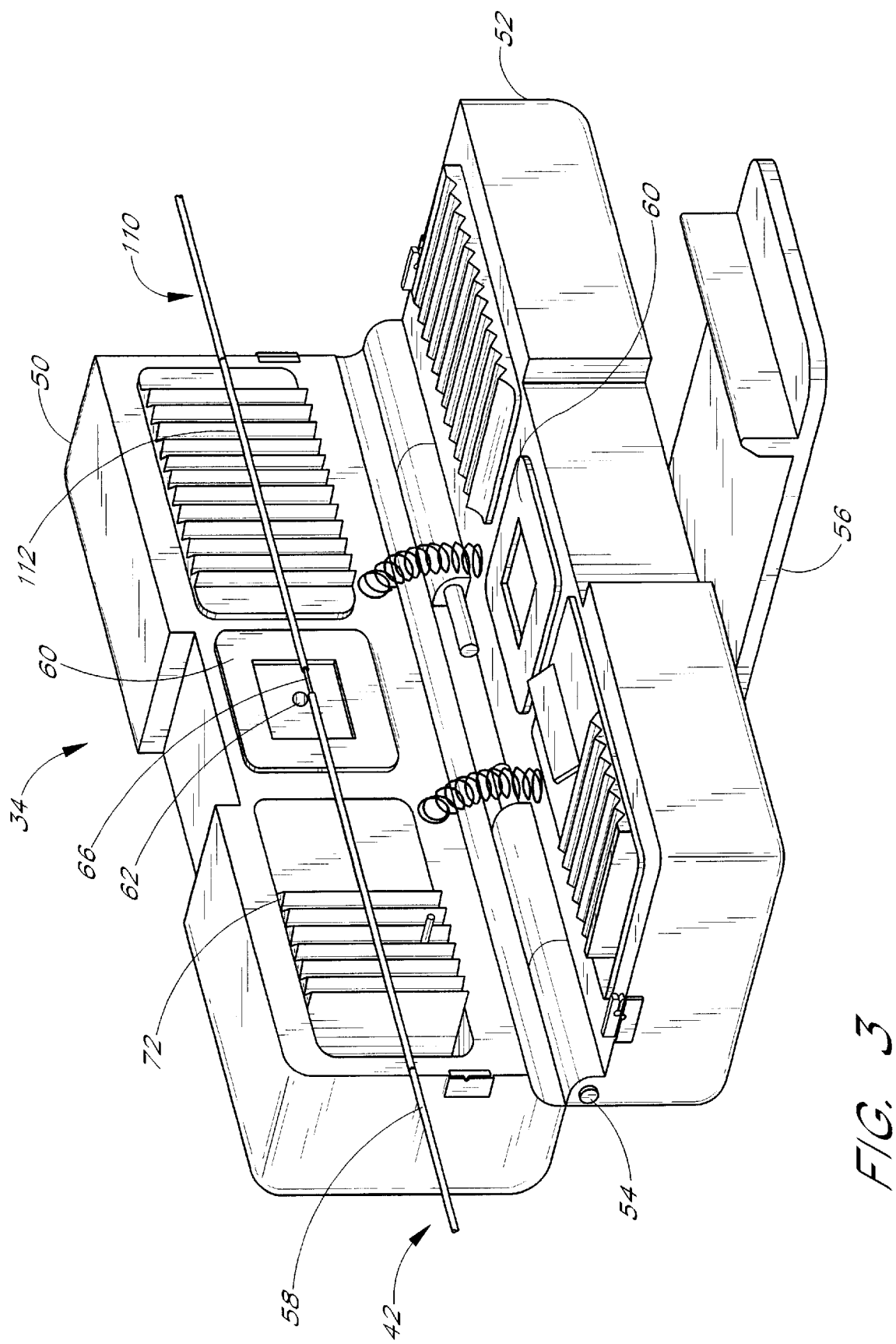
FIG. 3 shows a perspective view of the catheter valve and balloon catheter of FIG. 2 placed within an open inflation adapter.

FIGS. 2–4 illustrate the inflation/deflation of the occlusion balloon guidewire catheter shown in FIG. 1. As shown in FIG. 2, a syringe assembly 32 is connected to the occlusion balloon guidewire catheter 110 utilizing an inflation adapter 34. The syringe assembly 32, comprising the inflation syringe 36 and a larger capacity or reservoir syringe 38, is attached via tubing 40 to the inflation adapter 34 within which a low profile catheter valve 42 and the balloon catheter 110 are engaged during use.

The catheter valve 42, described in more detail below in connection with FIGS. 4A and 4B, is attached to an open proximal end of the catheter 110. The syringe 36 is used to inject inflation fluid through the adapter 34 and valve 42 into the lumen 118 of the hollow catheter 110, and into the balloon 122. The inflation adapter 34, described in more detail below in connection with FIG. 3, is used to open and close the valve 42 to regulate the inflation of the balloon 122 mounted on the distal end of the catheter 110.

More particularly, the balloon guidewire catheter 110 has a low profile catheter valve 42 attached to its proximal end having a side-access inflation port 120, shown in greater detail in FIGS. 4A and 4B. The inflation port 120, proximal end of the catheter 110 and distal end of the valve 42 are positioned within the inflation adapter 34 (see FIG. 3) to which syringe assembly 32 has been operably coupled. The inflation syringe 36 is coupled via an injection cap 44 at its distal end to a valve 46 that also connects the large capacity syringe 38 and a short tube segment 40. The tube segment 40 is adapted to connect to a fitting or male luer member 48 of the inflation adapter 34. Thus, the valve 42 is opened and closed by the adapter 34 to allow use of the low volume syringe 36 of the syringe assembly 32 to inflate the balloon 122 at the end of the catheter 110. Preferably, the low profile catheter valve 42 is as described in the above-referenced application LOW PROFILE CATHETER VALVE AND INFLATION ADAPTER, now U.S. Pat. No. 6,050,972, the entirety of which is incorporated by reference. It will be apparent especially from FIGS. 4A and 4B that the valve 42 is considered "low profile" since it is no larger in cross-sectional diameter than the catheter 110 itself.

Referring to FIGS. 2 and 3, the inflation adapter 34 comprises a housing having two halves 50, 52 preferably formed of metal, medical grade polycarbonate, or the like. The halves 50, 52 are attached by hinges 54 to be separated or joined in a clam shell manner. A locking clip 56 secures the halves while the adapter 34 is in use. A groove within the housing has a width to accept the proximal end 58 of the catheter 110 having the low profile valve 42. The male luer member 48 (FIG. 2), or other suitable connector, extends from a top of the housing to provide an inflation passageway. Seals 60 are provided within the housing and around the internal segment 62 of the inflation pathway to conduct the pressurized fluid provided by the syringe 36 attached to the male luer member 48.

In one embodiment shown in FIGS. 4A and 4B, the low profile catheter valve 42 comprises a movable sealer portion 64 attached at a distal end of a wire segment 66 and positioned within an inflation lumen 118 of the guidewire catheter 110. The wire 66 may be secured to a spring just within a proximal opening of the catheter 110. It will be noted that various spring or biasing arrangements may be utilized, including a zig-zag wire 68 which is formed on or replaces the wire segment and which provides biasing force to the sealer portion 64 due to frictional engagement with the walls of the lumen 118. The sealer portion 64 forms a fluid tight seal with the inflation lumen 118 by firmly contacting the entire circumference of a section of the inflation lumen 118. The sealer portion 64 may be positioned proximally of the side-access inflation port 120 on the catheter to establish an unrestricted fluid pathway between the inflation port 120 and the inflatable balloon 122 on the distal end. As desired, the clinician may move the sealer portion to a position at, or distal of, the inflation port, thereby preventing any fluid from being introduced into or withdrawn from the balloon 122 via the inflation port 120.

An actuator 70, shown in FIG. 2 at the top of the adapter housing, controls a cam which operates. sliding panels 72 (FIG. 3) contained in the housing. Preferably, the catheter 110 is positioned within the housing with the valve closed (FIG. 4B), such that the side inflation port 120 is located in the sealed inflation area 62 of the housing. It should also be appreciated that an adapter may be provided wherein the catheter 110 is positioned in the second half 52 of the adapter. An adjacent proximal portion of the catheter extends outside the housing (and the patient), and a proximal portion 58 of the catheter valve 42 extends out of the other side of the housing. The locking clip 56 is then secured and then the syringe 36 may be attached. The actuator 70 is moved from a first position to a second position, such that the sliding panels 72 within the housing cause the valve to be in an open position to allow fluid flow through the inflation port 120 (FIG. 4A). Closing the valve is accomplished by moving the actuator 70 from the second position back to the first position (FIG. 4B), such that the balloon inflation is maintained.

Other inflation adapter/inflation syringe assemblies may also be used. For instance, the adapter 34 can have additional features, such as a safety lock provided on the actuator knob 70 to prevent accidental opening when the adapter is being used and the catheter valve is open. In addition, the adapter can be provided with an overdrive system to overdrive a sealing member into a catheter. Details of these features and other inflation assemblies may be found in assignee's copending applications LOW PROFILE CATHETER VALVE AND INFLATION ADAPTER, application Ser. No. 08/975,723, filed Nov. 20, 1997, now U.S. Pat. No. 6,050,972, SYRINGE AND METHOD FOR INFLATING LOW PROFILE CATHETER BALLOONS, application Ser. No. 09/025,991, filed Feb. 19,1998, and LOW VOLUME SYRINGE AND METHOD OF INFLATING SURGICAL BALLOONS, application Ser. No. 09/195,796, filed Nov. 20, 1998, all of which are incorporated by reference in their entirety.

II. Balloon Catheter With Connecting Wires

FIG. 5 depicts a cross-sectional view of the distal portion of a balloon catheter 110 in one preferred aspect of the present invention, using the same reference numbers as in FIG. 1 for like components. This distal portion of the catheter generally comprises a balloon 122 mounted on the distal end 116 of tubular body 112, connecting wires 124, 126 mounted inside the balloon 122 to the distal end 116 of the tubular body 112 and extending distally therefrom, and a core wire 128 lying in substantially the same longitudinal axis as the tubular body and having a proximal end distally spaced from the distal end 116 of the tubular body outside the lumen 118. Coils 130, 132 surround the connecting wires and the core wire, respectively.

More particularly, at the distal end 116 of the tubular body 112, connecting wires are attached to the tubular body 112 and extend beyond the distal end. These wires may be attached either to the outside of the tubular body 112 or inside the lumen 118, by using adhesives, soldering, brazing, welding, or any other means known to those of skill in the art. Preferably, as shown in FIGS. 5 and 6A, two connecting wires 124, 126 are attached at their proximal ends 124A, 126A, respectively, to opposite sides of the outer wall of tubular body 112. These wires are preferably made of a metallic material, and more preferably are made of a material such as nitinol. Each wire preferably has a diameter of about 0.003 to 0.010 inches, and more preferably about 0.005 inches. The proximal ends 124A and 126A are preferably flattened as shown in FIG. 6A to form a better attachment with tubular body 112.

The connecting wires 124, 126 are illustrated as being substantially round over most of their length. The present inventors also contemplate that other shapes may be used. For instance, the wires 124, 126 may be ribbons having a substantially flattened configuration throughout.

Furthermore, it is not essential that two wires be used to connect the tubular body to the core wire. Thus, the core wire may be connected to the distal end of the tubular body through only one wire, or through three or more wires as well. Moreover, it is also contemplated that different means may be used to connect the tubular body to the core wire, such as through coils 130 and 132 alone, or by the balloon 122 itself.

As illustrated in FIGS. 5 and 6B, the two wires 124, 126 extend beyond the distal end of tubular body 112 for a length corresponding approximately to the length of the balloon 122. In FIG. 5, where the balloon 122 has a working length of about 5 mm, the wires 124, 126 extend in a longitudinal direction over a length of about 5 mm. These wires converge at their distal ends 124B, 126B near the distal end of balloon 122, where they are attached to core wire 128. At the connection point with the core wire 128, the wires 124, 126 are preferably attached at opposite sides of the proximal end 128A of the core wire and are preferably flattened at ends 124B, 126B, shown in FIG. 6C, in order to form a better connection to the core wire. The connection between the wires 124, 126 and core wire 128 is preferably made by adhesives, soldering, or a combination of the two.

The core wire 128 shown in FIG. 5 extends from a proximal end 128A at the attachment point of the core wire to the connecting wires to a distal end 128B. The proximal end 128A of the core wire 128 is preferably located within the interior of balloon 122 and near balloon distal end 122B. The core wire 128 may range in length from about 10 to 200 mm, more preferably from about 25 to 50 mm, and for most occlusive device applications, is typically about 35 mm. In the illustrated embodiment shown in FIG. 5, the length of the core wire 128 is about 30 mm, and has a diameter of about 0.007 inches. The core wire is preferably formed of a shape memory alloy such as nitinol, but may also be formed from other materials such as stainless steel. Other details regarding construction and design of the core wire may be found in assignee's copending application entitled CATHETER CORE WIRE, application Ser. No. 09/253,971, filed Feb. 22, 1999, now U.S. Patent No. 6,355,016, which is hereby incorporated by reference in its entirety.

As shown in FIGS. 5 and 6A–6C, a first coil 130 is provided within balloon 122 around the connecting wires 124, 126, and extends from the distal end 116 of tubular body 112 to a position adjacent the attachment of the connecting wires to the core wire 128. The coil 130 is mounted at its proximal end 130A over the flattened proximal ends 124A, 126A of connecting wires 124, 126, as well as over tubular body 112, as shown in FIG. 6A. The coil 130 is secured to the distal end of tubular body 112 by suitable means such as soldering, brazing or by an adhesive. One preferred adhesive type for connecting coil 130 to the tubular body 112 and wires 124, 126 is a cyanoacrylate. The coil 130 is formed of suitable radiopaque material, such as gold or platinum, or may be formed of nitinol or stainless steel. Preferably, the coil 130 is formed of stainless steel.

The coil 130 has a suitable outer diameter preferably of about 0.017 inches when the tubular body 112 at distal end 116 has an outer diameter of 0.014 inches. The length of coil 130 corresponds approximately to the working length of balloon 22, and is about 2 to 8 mm, more preferably, as shown in FIG. 5, about 5 mm.

As shown in FIG. 5, a second coil 132 is provided around the core wire 128. The second coil extends over substantially the entire length of the core wire, and as illustrated, is about 30 mm. This second coil 132 has an outer diameter of about 0.014 inches when the distal end of the tubular body 112 has a 0.014 inch outer diameter. This enables balloon inflation to be substantially uniform from proximal end 122A to distal end 122B. The first coil 130 overlaps the second coil 132 near the attachment point between the connecting wires and the core wire, as shown in FIG. 6C, and the two are preferably connected by adhesives, soldering, welding or brazing, as described above. Second coil 132 may be formed of similar materials as coil 130, and is preferably made of a radiopaque material. Coil 132 is preferably soldered to the core wire 128 at distal end 128B, forming a ball 134 at the distal end of the catheter. It should be appreciated that although two coils are described in the preferred embodiment, one coil by itself may suffice.

Balloon 122 is attached to the distal end 116 of the tubular body 112. More preferably, balloon 122 has a proximal end 122A mounted to the distal end 116 of the tubular body 112, and a distal end 122B mounted to the coils away from the distal end of tubular body 112. The proximal end 122A of the balloon 122 is secured to tubular body 112 by any means known to those of skill in the art, such as adhesives or heat bonding. As shown in FIG. 5, an adhesive 136 is used to connect the tubular body to the balloon 122. Adhesive 136 is preferably a cyanoacrylate. Similarly, at distal end 122B, the balloon 122 is secured to second coil 132 just distal to the overlap between coils 130 and 132 through the use of adhesive 136. Inflation of balloon 122 is provided by the passage of fluid through lumen 118 and through gaps in the coil 130. The wires 124 and 126 are preferably solder bonded or otherwise sealed at 152 to the proximal end of the core wire 128 and the coils 130 and 132 near the distal end 122B of the balloon to prevent inflation fluid from escaping from the distal end of the catheter.

Adhesives 136 applied to the proximal and distal ends 122A and 122B of balloon 122 wick into the balloon to form a bond with tubular body 112 and coil 132, respectively. To control the adhesion length of the balloon 122, optional adhesive stops 138, 140 are preferably provided on the tubular body 112 and coil 132. As illustrated in FIG. 5, an adhesive such as a proximal tube 138 is positioned around tubular body 112 and proximal to the coil 130 and connecting wires 124, 126. A distal tube 140 is provided over the coil 132 abutting against the distal 130B of coil 130. It should be appreciated that the adhesive stops may be provided at other locations of catheter 110, such as on coil 130. The adhesive stops 138, 140 preferably are positioned a desired distance from the proximal and distal ends of the balloon 122 to control the working length of balloon inflation. Thus, as illustrated in FIG. 5, where stops 138 and 140 have a length of about 0.25 mm, and balloon 122 has a length of about 9 mm, the stops 138, 140 are placed at about 2 mm from the proximal and distal ends of balloon 122 to create a working length of about 5 mm. The adhesive stops are preferably formed from a thermoset material such as polyimide. Other details not necessary to repeat here regarding the adhesive stops may be found in the above-referenced application entitled BALLOON CATHETER AND METHOD OF MANUFACTURE, application Ser. No. 09/026,225, filed on Feb. 19, 1998.

Proximal to the connection of the balloon 122, coil 130, and connecting wires 124, 126 to the distal end of the tubular body 112, a radiopaque marker or coil 142 is provided on the tubular body. However, an embodiment is also contemplated where because the coils 130, 132 are made of radiopaque material such as gold or platinum, there is no need for the marker 142. As shown in FIG. 5, the marker 142 is preferably in the form of a tube surrounding the tubular body 112. An adhesive taper 144 is provided over the marker 142 at the proximal end connecting the tubular body to the balloon. Preferably, a cyanoacrylate adhesive is used, although other similar materials may be used as well. The taper 144 extends from the proximal end 122A of the balloon 122 to the tubular body 112. A similar taper 146 is provided from the distal end of the balloon 122 connecting the balloon 122 to the second coil 132. Other details regarding these features may be found in the above-referenced application entitled SHAFT FOR MEDICAL CATHETERS, application Ser. No. 09/026,105, filed Feb. 19, 1998.

The tubular body 112 of FIG. 5 preferably exhibits a diameter reduction near distal end 116. In the illustrated embodiment, the tubular body 112 has an outer diameter of about 0.018 inches at proximal end 114 (not shown), and maintains a constant diameter substantially throughout the length of the tubular body 112 until near to distal end 116. At about 5 to 30 cm from distal end 116, the outer diameter of tubular body 112 decreases from about 0.018 inches to about 0.014 inches. This section of decreasing diameter preferably extends over a length of about 1 to 25 cm. At distal end 116, the tubular body 112 has a section of constant cross-section, which as illustrated, is about 5 to 29 cm in length.

The dimensional decrease in diameter of tubular body 112 is provided to minimize the profile of catheter 110 to provide for easier and safer advancement of catheter 110 into the vasculature of a patient. Specifically, with balloon 122 mounted to distal end 116, the maximum profile of the catheter 110 during advancement depends on the uninflated outer diameter of balloon 122. By making the distal end of tubular body 112 relatively smaller than the rest of the tubular body, mounting of the balloon 122 on distal end 116 does not significantly increase the profile of the catheter, as compared with the size of the proximal end of the device. The 0.018 inch hypotube provides a stiffer shaft for better pushability and support of larger PTCA devices, especially for bulky stent delivery systems. Also, with a larger outer diameter, the inner diameter may be increased which reduces the inflation and deflation times. It should be appreciated, however, that the tubular body 112 can have a constant diameter therethrough. Optionally, the distal end of the tubular body may also or alternatively be softened in a salt bath to improve flexibility by heat treating the tube.

Catheter 110, described in FIGS. 5 and 6A–6C above, offers significant improvements in flexibility and balloon centering at the distal end of catheter 110. In particular, this design offers a better transition between the tubular body 112 to balloon 122 to tip 134. By placing the proximal end of the core wire beyond the distal end of the tubular body, the catheter possesses a transition region between the tubular body and the core wire formed in part by connecting wires found inside the balloon 122 and coil 130. The coil 130 gives the catheter 110 flexibility while the wires 124, 126 add structure and support. Thus, the flexibility of the catheter gradually increases from the tubular body 112, through the balloon 122, to the core wire 128.

Balloon centering is improved because the reduction of stress concentration points in the balloon leads to a more uniform expansion. In particular, mounting the balloon over a flexible member allows the balloon to expand more uniformly by more equally distributing stresses within the balloon wall. In addition, the uniform expansion of the balloon reduces localized thinning of the balloon ;which may cause premature rupture or balloon failure.

III. Coaxial Core Wire

FIGS. 7 and 8 illustrate another preferred aspect of the distal end of a balloon catheter 110, wherein catheter 110 has improved flexibility characteristics at its distal end. For ease of understanding, reference numbers used in FIGS. 7 and 8 correspond substantially to the reference numbers used in FIGS. 1 and 5–6C. The tubular body 112 as shown in FIG. 7 is preferably substantially the same as described in the embodiment with respect to FIG. 5, specifically wherein tubular body 112 has an outer diameter of about 0.018 inches over a substantial portion of its length from proximal end 114, and reduces to an outer diameter of about 0.014 inches at distal end 116. However, it should be appreciated that the design described herein could be used for a tube with a constant outer diameter, for instance of about 0.014 inches, along the entire length of the tubular body 112. A core wire 128 is inserted into the distal end of the tubular body 112 and extends out of the lumen 118 in a distal direction therefrom. Coils 130, 132 are provided surrounding core wire 128, and balloon 122 is mounted over the coils to the distal end of tubular body 112.

More particularly, as illustrated in FIG. 7, the proximal end 128A of the core wire 128 extends into the lumen 118 of tubular body 112 but is not attached to the tubular body, thereby creating an annular space between the tubular body 112 and the core wire 128. The annular space extends around the core wire over the entire length of the core wire that is positioned inside the lumen 118. The proximal end of the core wire 128 preferably extends into the lumen 118 at distal end 116 for a distance of about 2 to 200 mm, and more preferably about 7 mm. The core wire 128 extends from its proximal end 128A to its distal end 128B over a length of about 20 to 200 mm, and more preferably, from about 25 to 50 mm, and for most occlusive devices, about 35 mm. As shown in FIG. 7, the core wire 128 has a length of about 45 mm. The core wire preferably has a diameter of about 0.003 inches extending over its distal length 128B, although it will be appreciated that a tapered core wire may be used as well. The core wire is preferably formed of nitinol, although stainless steel or any other suitable materials may also be used.

The first coil 130 is attached to the distal end of the tubular body 112 and extends distally therefrom to surround core wire 128. Coil 130 is preferably made of nitinol, although materials such as stainless steel, gold or platinum, may also be used. The coil 130 has an outer diameter preferably of about 0.017 inches, and preferably extends over a length of about 5 mm from the distal end of tubular body 112, corresponding approximately to the working length of balloon 122. Coil 130 is attached to tubular body 112 by soldering, brazing, or an adhesive. One preferred adhesive is a cyanoacrylate, although as will be appreciated by those of skill in the art, other similar adhesives adapted to form metal-to-metal bonds may be used.

The second coil 132 extends from the distal end of the first coil 130 in a distal direction surrounding core wire 128. The second coil 132 is attached to the inside of the first coil 130, and bonded by soldering or a similar technique. Alternatively, a butt joint could be used if the coils 130 and 132 are of the same or similar dimensions. The coil 132 extends over the core wire 128 to the distal end 128B of the core wire, where the coil 132 is soldered into a ball 134. As illustrated in FIG. 7, coil 132 extends over a length of about 30 mm and has an outer diameter of about 0.014 inches. The coil 132 is preferably made of radiopaque materials such as platinum, although other materials such as nitinol, gold and stainless steel may also be used.

The balloon 122 is attached to the tubular body 112 such that its proximal end 122A is mounted on the distal end 116 of the tubular body and the distal end 122B of the balloon is mounted on the coil 132, away from the tubular body. Conventional balloon bonding techniques may be used to mount the balloon 122 to the tubular body 112, including adhesive bonding or heat bonding, as known to those of skill in the art. As shown in FIG. 7, the proximal end 122A of the balloon 122 is bonded to the tubular body 112 by an adhesive 136. One preferred adhesive type is a cyanoacrylate. Although the balloon 122 is shown as bonded directly to tubular body 112, the balloon may also be indirectly mounted through adhesive bonding to coil 130. The distal end 122B of balloon 122 is bonded by the adhesive 136 to second coil 132, which in turn is bonded to the core wire 128. Although the adhesive 136 as shown is provided primarily over the second coil 132, the adhesive 136 may also be provided over the first overlapping coil 130. Furthermore, it is, also contemplated that only one coil, rather than two, may be used. The balloon 122 is preferably mounted such that the interior or working area of the balloon is substantially distal to the tubular body 112. Then, inflation of the balloon may occur through passage of fluids through gaps in coil 130. As described with respect to FIG. 5 above, a plug 152 is preferably provided between the coil 132 and core wire 128 at the proximal end 132A to prevent fluids from escaping the balloon 122.

Optional adhesive stops 138, 140, as described with respect to FIGS. 5–6C above, are preferably provided over the tubular body 112 and coil 132, respectively, to prevent adhesive 136 from wicking into the balloon 122 beyond the point of the stops. The adhesive 136 wicks into the balloon 122 over a distance preferably of about 2 mm at each end. Thus, when the balloon length is about 9 mm, the balloon has a working length of about 5 mm. It should be appreciated that the stops 138, 140 may be provided at other locations on the catheter.

The embodiment shown in FIG. 7 also preferably includes a radiopaque marker 142 mounted on the distal end of the tubular body 112 proximal to the point where the balloon attaches to the tubular body, as described above. This marker is covered by an adhesive taper 144 which forms a gradual connection between the tubular body and the proximal end of the balloon. Similarly, an adhesive taper 146 is provided at the distal end of the balloon 122 from the distal end 122B to the coil 132, as described in further detail above.

The catheter described in FIG. 7 above offers improved flexibility and balloon properties due in part to the fact that the proximal end of the core wire is not bonded or fixed to the tubular body 112 or any other part of the catheter. Rather, the proximal end 128A is coaxial with the tubular body and thus "floats" within the tubular body 112. This improves flexibility because the proximal end of the core wire may move longitudinally within the tubular body when the distal end of the catheter is bent while it is moved through a patient's vasculature. Furthermore, when balloon 122 is inflated, longitudinal expansion of the balloon is not hindered by the core wire being fixably mounted within the tubular member 112. Thus, as the balloon expands the core wire moves distally. This reduces the stress placed on the balloon to improve the balloon's rupture properties. Balloon centering is similarly improved because the reduction of stress concentration points in the balloon leads to a more uniform expansion.

FIG. 8 shows an alternative embodiment of the coaxial core wire 128 within tubular body 112. In this embodiment, the catheter contains a stopping mechanism to prevent the proximal end 128A of the core wire from sliding completely out of the lumen 118 of tubular body 112. For instance, tubular body 112 may have an increased wall thickness at distal end 112, or the lumen 118 may be partially blocked at distal end 116. Then, providing core wire 128 with a dimensional increase at proximal end 128A, the core wire 128 will be prevented from escaping the lumen 118 because the dimension of the lumen 118 distal to the proximal end of the core wire is less than the dimension of the proximal end of the core wire.

As shown in FIG. 8, the tubular body 112 may be crimped near its distal end 116 and over the core wire proximal end 128A. This crimp 148 is not substantial enough to actually contact the core wire 128 when centered within the lumen 118 of the distal end 16. However, the core wire proximal end 128A is provided with a handle 150 which has a diameter greater than the inner diameter of lumen 118 at the crimp 148. The handle 150 also keeps the core wire centered in the lumen 118. The handle 150 thereby prevents the core wire from moving longitudinally within the tubular body 112 beyond the location of crimp 148. The handle 150 is located preferably about 5 to 20 mm from the crimp 148. Where the core wire diameter is about 0.004 inches, the handle preferably has a diameter of about 0.006 inches, and the distance between opposite sides of crimp 148 is preferably about 0.005 inches.

The crimp 148 is preferably located about 1 mm from the distal end of the tubular body 112. In the embodiments where tubular body 112 is made of nitinol, sufficient crimping pressure must be exerted upon the tubular body to overcome the elastic response of the nitinol. Generally this requires exertion of sufficient pressure to deform the nitinol tubular body by about 9% or more. Where a nitinol tubular body has an outer diameter of 0.014 inches and an inner diameter of about 0.0095 inches, it has been found that a pressure of about 120 ksi is sufficient. Other pressures may also be used provided that they are sufficient to cause tubular body 112 to form an indentation over the core wire, but not so great as to actually contact the core wire and interfere with its longitudinal movement within the tubular body. Further details regarding crimping may be found in the above-referenced application entitled CATHETER CORE WIRE, application Ser. No. 09/253,971, filed Feb. 22, 1999.

Figures 9A, 9B:
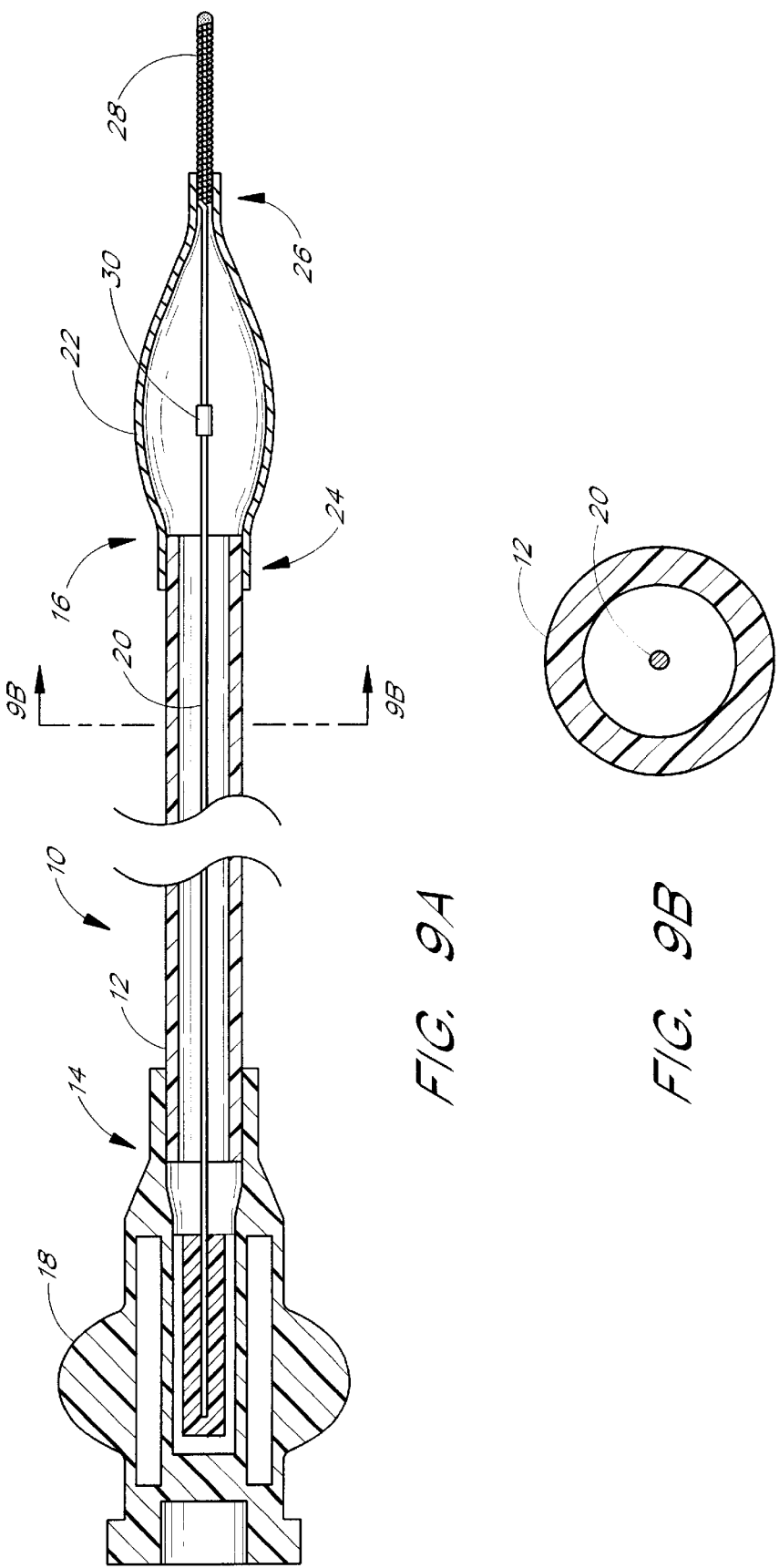
FIGS. 9A and 9B are cross-sectional views of a catheter having a core wire mounted at its proximal end to an adapter and at its distal end to an inflation balloon.
Figure 10:
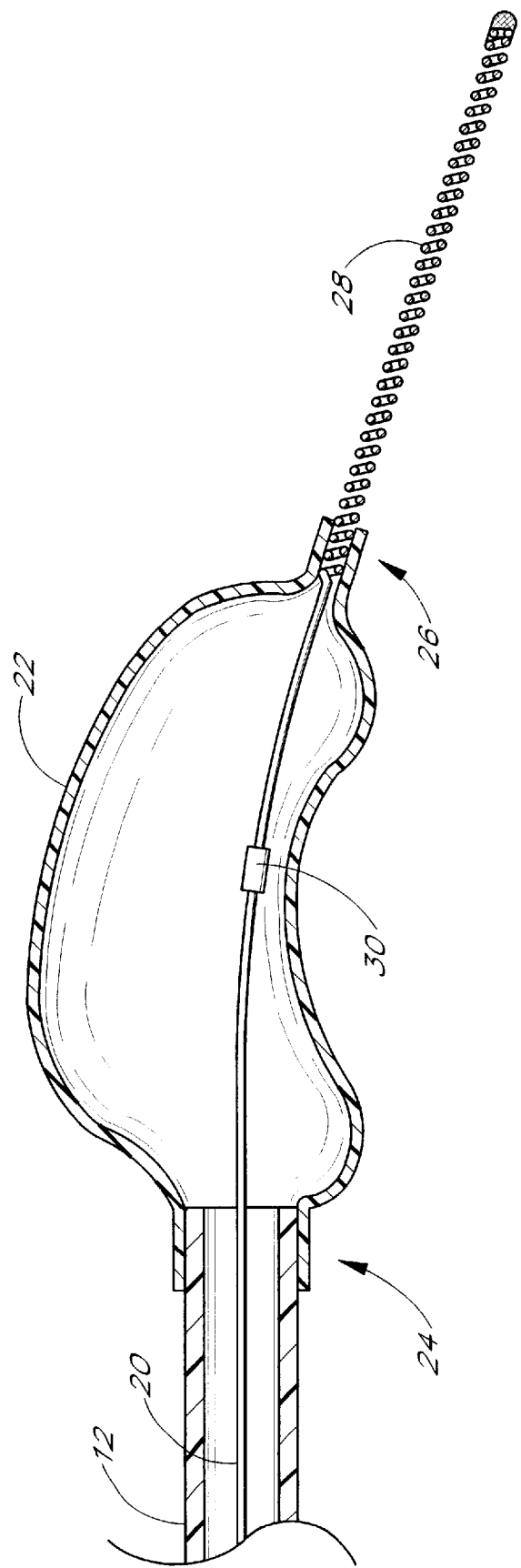
FIG. 10 is a cross-sectional view of the balloon and core wire of FIG. 9A, with the balloon shown in an inflated state exhibiting bowing.

The problem of bowing is due to balloon inflation is further illustrated with respect to FIGS. 9–10. FIGS. 9A and 9B show a catheter 10 having a tubular body 12 extending from a proximal end 14 to a distal end 16. An adapter 18 is mounted to the proximal end of the tubular body 12, and a core wire 20 is mounted to the catheter within adapter 18 at the proximal end. A balloon 22 is mounted to the distal end 16 of the tubular body, and more specifically the balloon 22 is mounted at its proximal end 24 to the tubular body and at its distal end 26 to the core wire 20 which extends through the balloon. A marker 30 is placed on the core wire 20 within the balloon 22, and coils 28 extend from the distal end of the balloon.

The problem with this configuration is that the core wire 20 is fixed longitudinally at both its proximal end and its distal end. When balloon 22 is inflated, the balloon expands not only radially, but also longitudinally, causing the bowing effect shown in FIG. 10 because both ends of the balloon are effectively fixed. This problem also occurs in devices where the proximal and distal ends of the balloon are both mounted to the same hypotube, or any other device in which the ends of the balloon are held in fixed relation.

FIG. 11A shows an alternative embodiment of a catheter 200 having a floating core wire therein to solve the bowing problem described above. Catheter 200 comprises an elongate tubular body 202 extending between a proximal end 204 and a distal end 206. A lumen 208 extends through the tubular body to provide a fluid passageway from the proximal end to the distal end. A balloon 210 is mounted to the distal end 206 of the tubular body. Coils 212 extend from the distal end of the balloon into a rounded tip 214 at the distal end of the catheter. A core wire 218 extends from the proximal end 204 of the tubular body 202 through the distal end 206 and into the balloon 210, terminating at the start of the coils 212. A radiopaque marker 220 is provided on the core wire 218 for visualizing the catheter 200.

Figure 12A:
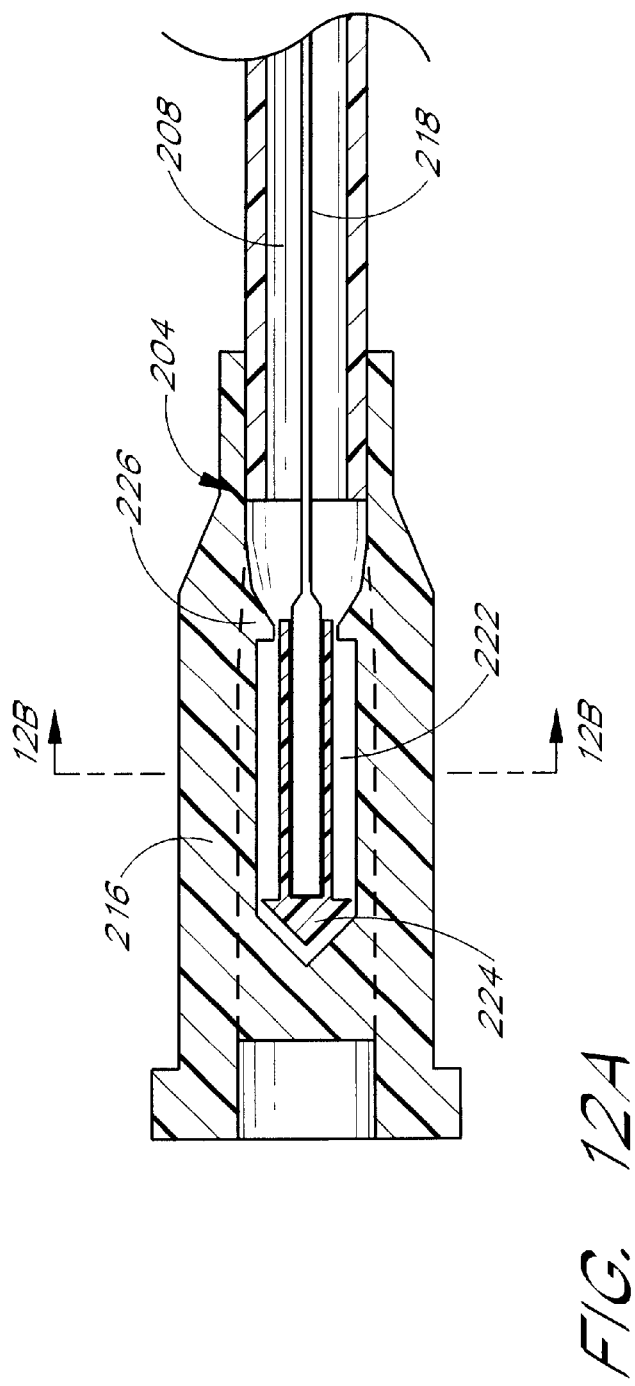
FIG. 12A is an enlarged cross-sectional view of the proximal end of the catheter shown in FIG. 11A.
Figure 12B:
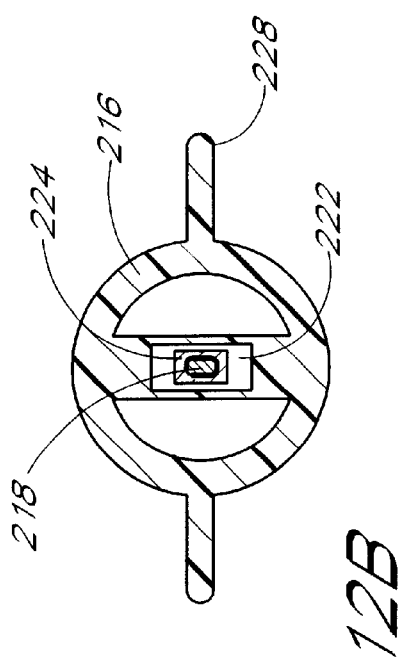
FIG. 12B is a cross-sectional view of the proximal end of the catheter of FIG. 12A through line 12B—12B.

At the proximal end of the catheter 200, as shown in FIG. 12A, the core wire 218 extends into an adapter 216 into a chamber 222. The adapter 216 is used for inflating the balloon 210 through lumen 208 and also for torquing the device through use of arms 228. The proximal end of the core wire is preferably flattened, as shown in FIG. 12B. This configuration provides an effective locking mechanism to the adapter which is important when torquing the adapter to maneuver the distal tip of the catheter. The proximal end of the core wire further includes an increased dimension such as protruding head 224 which serves to lock the proximal end of the core wire inside the chamber 222 during balloon inflation. More particularly, as shown in FIGS. 11A–12A, the core wire has an arrowhead shaped proximal end 224 which, in conjunction with the smaller dimension of the chamber distal to the proximal end 224, keeps the arrowhead 224 in the chamber 222. As shown in FIG. 12A, the smaller dimension of the chamber 222 distal to proximal end 224 can be provided with flanges 226 located at the distal end of the chamber.

As shown in FIG. 11B, when balloon 210 is inflated, the balloon expands longitudinally from a length of $L_1$ to $L_2$. This longitudinal expansion causes the core wire 218 to advance distally within the lumen 208, but no further than substantially the length of the chamber 222. This longitudinal movement also provides improved flexibility during navigation as described above.

III. Longitudinally Flexible Hypotube

In another embodiment of the present invention, a balloon catheter 300 is provided having unique flexibility characteristics particularly in the area where the balloon is mounted. As shown in FIG. 13A, the catheter 300 comprises a tubular body 312 having a proximal end 314 (not shown) and a distal end 316 and a lumen 318 extending therethrough. An expandable member such as a compliant inflatable balloon 322 is mounted to the distal end 316 of the tubular body, preferably such that both the proximal end 322A and distal end 322B of the balloon are both mounted to the tubular body 312. A core wire 328 is provided inside the lumen 318 at the distal end 316 of the tubular body and extends distally therefrom. Coils 332 extend from the distal end 316 surrounding core wire 328, and terminate in a distal ball 334.

The tubular body is preferably made from a nitinol material such as described above. A distal section of the tubular body 312 is configured to axially expand in response to expansion of the expandable member. More preferably, for the balloon catheter shown in FIG. 13A, a distal section of the tubular body 312 is given desired flexibility within the balloon area using special cuts 352 made in the wall of the tubular body. These cuts 352 are preferably made using a laser, although other methods, such as machining and EDM, may also be used. In the preferred embodiment shown in FIG. 13A, the distal section of the tubular body 312 has a coiled configuration. However, it should be appreciated that the hypotube may be cut or configured in a variety of different ways to provide desired flexibility.

For the embodiment shown in FIG. 13A, the cuts 352 in the hypotube providing the coiled configuration preferably begin about 1 to 3 mm from the distal end 316, and extend proximally therefrom corresponding approximately to the length of the balloon 322 or further, depending on the desired flexibility. For example, for a balloon with a length of about 8 mm, cuts may be made over a length of about 2 to 20 mm. In embodiments where more flexibility is needed only near the distal end of the hypotube, the cuts may be provided over a shorter length, for example, about 2 to 3 mm. Similarly if more flexibility is desired at the proximal end of the balloon or even beyond, cuts may be made in the tubular body over a length of 15 mm or more.

The hypotube coils may have a constant or a variable width and/or pitch to control the flexibility of the catheter. For the embodiment shown in FIG. 13A, the tubular body 312 is cut starting from about 2 mm from the distal end 316 of the hypotube and extending beyond the proximal end of the balloon 322 over a total length of about 15 mm. At the distal end of the cuts 352, the coils in the tubular body 312 have a ribbon width $W_1$ of about 0.15 mm, which gradually increases proximally to a ribbon width of about 1 to 2 mm at the proximal end of the cuts. The angle of the cuts 352 relative to the longitudinal axis of the hypotube preferably increases distally as shown in FIG. 13A to further increase the flexibility. toward the distal end. In the preferred embodiment, at the distal end of the cuts the angle is about 80°, which gradually decreases to about 3° at the proximal end of the cuts. Over the entire coiled section, the hypotube cuts preferably have a pitch of about 0.08 mm. The advantage of the variable ribbon width is that it provides a more gradual transition between the tubular body 312 and the core wire 328. Furthermore, by gradually decreasing the angle of the cut proximally, the coiled tubular body has greater tensile strength as the cut angle decreases.

Figure 14:
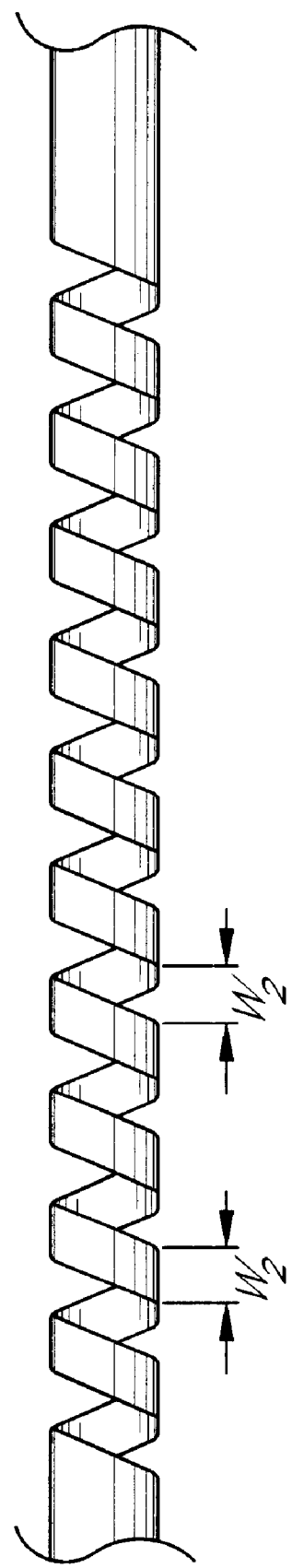
FIG. 14 is a side view of a coiled hypotube having a constant ribbon width and pitch.

It should be appreciated that further variations in the length, width, pitch and angle of the coiled tubular body are also contemplated. For example, coils of constant width and pitch $W_2$ of about 0.25 mm may be used, as shown in FIG. 14. Furthermore, the coiled hypotube can be made by starting the coil with a cut depth at a proximal location that does not extend entirely through the wall of the tubular body, and gradually increasing the depth distally until the hypotube is completely cut through. Such an embodiment is shown in FIGS. 15A and 15B. In addition, the distal section of the tubular body 312 may also be given a special heat treatment to further impart flexibility. For example, in one embodiment, the distal about 30 mm of the tubular body 312 may be heat treated to improve flexibility.

In constructing the catheter 300 of the preferred embodiment, after the tubular body 312 is cut into the desired configuration, the core wire 328 is prepared for mounting inside the distal end 316 of the tubular body 312 as shown in FIG. 13A. The preferred core wire 328 is made of a nitinol material and has a proximal end 328A (not shown) and a distal end 328B. As shown in FIGS. 16A–16D, this core wire 328 preferably has five sections: a proximal first section 370 having a substantially constant diameter, a tapered second section 372, a third section 374 having a substantially constant diameter, a tapered fourth section 376 and a fifth section 378 having a flattened distal tip. As illustrated in FIG. 16A, for the preferred embodiment, the first section 370 preferably has a diameter of about 0.005 to 0.006 inches and a length of about 10 mm. The second section, 372 is tapered over a length of about 6 mm, and increases in diameter from about 0.005 to 0.006 inches to about 0.007 inches. The third section 374 has a substantially constant diameter of about 0.007 inches and a length of about 4 mm. The distal end of this third section aligns with the distal end 316 of tubular body 312. The fourth section 376 tapers over a length of about 13 to 15 mm to flattened tip 378, which has a length of about 10 mm and a thickness of about 0.002 inches. Within section 378, an additional taper is provided at transition 380 such that the flat distal tip decreases proximally in thickness to provide a more gradual transition between the thin flat section 378 and the round tapered section 376. This transition 380 preferably has relatively flat surfaces and a length of about 3 to 5 mm.

Other details not necessary to repeat here may be found in the above-referenced CATHETER CORE WIRE, application Ser. No. 09/253,971, filed Feb. 22, 1999. It should be appreciated that core wires having differing lengths and constructions may also be used for the catheter 300. Thus, a core wire may be provided having only one of the proximal or distal tapers, multiple proximal and distal tapers, or no taper at all. Furthermore, the core wire 328 may be provided without first and second sections 370 and 372 such that substantially all of the core wire 328 extends out of the distal end 316. Moreover, a core wire may be provided having a proximal taper directly adjacent a distal taper.

Preferably, the coils 332 are soldered to the core wire and extend from the start of the distally tapered section 376 to the distal end of the flattened tip 378. Thus, for the core wire of the preferred embodiment, the coils 332 extend over a length of about 25 mm. After constructing this coil/core wire subassembly, the core wire 328 is inserted into the lumen 318 of the tubular body 312 such that the beginning of the distal taper in section 376 corresponds with the very distal end 316 of the tubular body and the coils 332 butt against the distal end 316. The core wire 328 is preferably attached to the tubular body 312 in middle section 374 by crimping at one or more points, more preferably at points 362 and 364 as shown in FIG. 13A. Crimping of the tubular body 312 to the core wire 328 can be accomplished using crimping pressures of about 120 ksi or other pressures, as described above. In addition to or in place of crimping, the core wire 328 may also be attached to the tubular body 312 by soldering, adhesives or epoxy, or by any other methods known to one skilled in the art.

The core wire 328 extends proximally into the tubular body 312 through the area where the hypotube is cut. The length that the first, second and third sections 370, 372 and 374 extend into the tubular body 312 is preferably between about 10 and 100 mm, more preferably about 15 to 60 mm, and in the preferred embodiment illustrated in FIG. 13A and 16A, about 20 mm. The length that the core wire 328 extends out of the lumen 318 is preferably about 10 to 200 mm, more preferably about 15 to 60 mm, and as illustrated in FIG. 13A, about 25 mm. By extending the core wire proximally into the hypotube, the core wire provides additional structural support to the catheter. However, because the preferred core wire is proximally tapered, the core wire 328 does not contact the inner wall of the tubular body 312, and therefore, does not substantially interfere with the ability of the catheter to traverse turns in a blood vessel or with the inflation of the balloon.

As shown in FIG. 13A, the balloon 322 is mounted to the distal end of the tubular body, the balloon 322 having a proximal end 322A and a distal end 322B which are both mounted to the tubular body. The balloon 322A of the preferred embodiment has a length of about 8 mm, an outer diameter of about 0.034 inches and an inner diameter of about 0.015 inches. As shown in the preferred embodiment of FIG. 13B, the cuts 352 are made such that they extend outside of the working area of balloon 322 and also proximally of the balloon. A sleeve 366 is preferably provided over the tubular body 312 and the cuts 352 proximal to the balloon working area to prevent inflation fluid from escaping the lumen 318. The sleeve is preferably a shrink tube made of PET, FEP, TFE or a similar material. In the preferred embodiment, this shrink tube has a length of about 15 mm and extends proximally starting from about 5 mm from the distal end 316. This shrink tube therefore allows cuts to be made proximally of the working area of the balloon for added flexibility without allowing fluid to escape. Alternatively, when proximal cuts do not extend all the way through the tubular body wall, as in FIG. 15B, or when there are no cuts proximal to the balloon at all, no shrink tube is needed.

The balloon 322 is preferably made from a C-Flex material or other compliant material and is attached to the tubular body 312 by adhesives or other means as described above. Adhesives stops 338 and 340 are provided about 2 mm from the ends of the balloon, as described above, to control the wicking length of the adhesive 336 into the balloon working area. Balloon inflation is provided through the cuts in the tubular body 312.

The preferred embodiment shown in FIG. 13A also includes a coiled marker 342 mounted to the tubular body 312 proximal of the balloon 322. By making the marker 342 coiled, this design provides added flexibility to the balloon section of the distal end. The coil 342 is preferably made of platinum or a similar material, with an outer diameter of about 0.024 inches, an inner diameter of about 0.016 inches, and a length of about 1 mm. As shown in FIG. 13A, the coiled marker 342 preferably butts against the balloon 322. It should be appreciated that while the marker 342 is described as coiled, the marker may also be cut or configured in other manners to provide improved flexibility.

Adhesive tapers 344A, 344B and 346 are provided adjacent the balloon to provide a transition region between the tubular body 312 and :balloon 322 at the proximal end 322A and between the balloon 322 and the core wire 328 at the distal end 322B. The distal taper 346 therefore extends from the distal end of the balloon to the core wire 328. The taper materials are preferably made of cyanoacrylate adhesives, such as described above, or softer adhesives, such as UV curable or modified adhesives. In the embodiment shown in FIG. 13A, the taper 344A is preferably a cyanoacrylate adhesive, and the adhesives 344B and 346 are preferably UV adhesives. The distance between the proximal end of taper 344A and proximal end 322A is preferably about 1 to 3 mm, more preferably less than about 2.5 mm, with the taper 344A itself preferably having a length of less, than about 1 mm. However, a single taper could also be used as described above. The length of the distal taper 346 is preferably about 3 mm. Other details not necessary to repeat here may be found in the above-referenced BALLOON CATHETER AND METHOD OF MANUFACTURE, application Ser. No. 091026,225, filed on Feb. 19, 1998, and SHAFT FOR MEDICAL CATHETERS, application Ser. No. 09/026,105, filed Feb. 19, 1998.

Inflation of the balloon 322 in FIG. 13A causes the coils in the hypotube to expand longitudinally in accommodation of the longitudinal expansion of the balloon. This expansion uniformly distributes stresses in the balloon, leading to better rupture properties and balloon centering. The present inventors have witnessed, for example, longitudinal growth of the hypotube typically of about 2 to 4 mm due to balloon expansion, and as much as about 10 to 20 mm. Moreover, because the sections 370, 372 of the core wire proximal to the crimps 362 and 364 does not contact the inner wall of the tubular body 312, the core wire 328 does not interfere with the balloon's longitudinal expansion.

It should be understood that certain variations and modifications of this invention will suggest themselves to one of ordinary skill in the art. The scope of the present invention is not to be limited by the illustrations or the foregoing descriptions thereof, but rather solely by the appended claims.

What is claimed is:

1. A catheter, comprising:
   an elongate tubular body having a proximal section and a distal section and a lumen extending therethrough; and
   an expandable member connected to the distal section, the expandable member having a proximal end and a distal end;
   wherein the elongate tubular body includes a coiled section in the distal section of the tubular body, the coiled section beginning at a location proximal to any expandable member connected to the tubular body, extending past the proximal end of the expandable member, and terminating at a point along the elongate tubular body between the proximal and distal ends of the expandable member.

2. The catheter of claim 1, wherein the expandable member is a compliant inflatable balloon.

3. The catheter of claim 1, wherein both the proximal end and the distal end of the expandable member are mounted to the tubular body.

4. The catheter of claim 1, wherein the coiled section is formed by laser cutting a solid hypotube.

5. The catheter of claim 4, wherein the elongate tubular body is metallic.

6. The catheter of claim 5, wherein the elongate tubular body is made of nitinol.

7. The catheter of claim 1, wherein the coiled section has a decreasing ribbon width toward a distal end of the tubular body.

8. The catheter of claim 1, further comprising a sleeve provided partially over the coiled section to prevent fluid from escaping the lumen through the coiled section, the sleeve having a proximal end that is proximal to the proximal end of the coiled section and a distal end that is proximal to the distal end of the coiled section.

9. The catheter of claim 1, further comprising a radiopaque marker that surrounds the tubular body at a location proximal the expandable member.

10. The catheter of claim 1, wherein the marker has a coiled configuration.

11. A catheter, comprising:
   an elongate tubular body having a proximal end and a distal end and a lumen extending therethrough, wherein the tubular body near its distal end has a coiled section with a proximal end and a distal end to provide the tubular body with longitudinal flexibility;
   an inflatable member having a proximal end and a distal end mounted to the tubular body, the proximal end being mounted between the proximal and distal ends of the coiled section and the distal end being mounted distal to the coiled section; and
   a non-inflatable tubing provided over the tubular body, the tubing having a proximal end that is proximal to the proximal end of the coiled section and distal to the proximal end of the tubular body, and a distal end that is proximal to the distal end of the coiled section;
   wherein the inflatable member is capable of being inflated by fluid travelling through the lumen of the tubular body and passing through the coiled section at its distal end, distal to the tubing, into the inflatable member.

12. A catheter, comprising:
   an elongate tubular body having a proximal section and a distal section and a lumen extending therethrough;
   an expandable member connected to the distal section, the expandable member having a proximal end and a distal end;
   wherein the elongate tubular body includes a coiled section only in the distal section of the tubular body, the coiled section beginning at a proximal end that is proximal to the expandable member, extending distally therefrom, and terminating at a distal end inside the expandable member between the proximal and distal ends of the expandable member; and
   a sleeve provided partially over the coiled section to prevent fluid from escaping the lumen through the coiled section, the sleeve having a proximal end that is proximal to the proximal end of the coiled section and a distal end that is proximal to the: distal end of the coiled section.

13. The catheter of claim 12, wherein the expandable member is a compliant inflatable balloon.

14. The catheter of claim 12, wherein both the proximal end and the distal end of the expandable member are mounted to the tubular body.

15. The catheter of claim 12, wherein the elongate tubular body is metallic.

16. The catheter of claim 15, wherein the elongate tubular body is made of nitinol.

17. The catheter of claim 12, wherein the coiled section has a decreasing ribbon width toward a distal end of the tubular body.

18. A catheter, comprising:
   an elongate tubular body having a proximal section and a distal section and a lumen extending therethrough; and
   a single expandable member connected to the distal section, the expandable member having a proximal end and a distal end;
   wherein the elongate tubular body includes a coiled section in the distal section of the tubular body, the coiled section beginning at a location near the distal end of the elongate tubular body and proximal to the single expandable member, extending past the proximal end of the expandable member, and terminating at a point along the elongate tubular body.

19. The catheter of claim 18, wherein the single expandable member is an inflatable balloon.

20. The catheter of claim 18, further comprising a sleeve provided partially over the coiled section to prevent fluid from escaping the lumen through the coiled section, the sleeve having a proximal end that is proximal to a proximal end of the coiled section and a distal end that is proximal to a distal end of the coiled section.

21. The catheter of claim 18, wherein both the proximal end and the distal end of the expandable member are mounted to the tubular body.

22. The catheter of claim 18, wherein the elongate tubular body is metallic.

23. The catheter of claim 22, wherein the elongate tubular body is made of nitinol.

24. A catheter, comprising:

an elongate tubular body having a proximal section and a distal section and a lumen extending therethrough; and an expandable member having a proximal end and a distal end that are both connected to the distal section of the tubular body wherein the expandable member is an inflatable balloon;

wherein the tubular body has a coiled section only in the distal section of the tubular body and extending at least partially within the expandable member to impart the tubular body with longitudinal flexibility at least in the portion of the tubular body within the expandable member, the coiled section including at least a portion having a variable width between the turns of the coil, and a sleeve provided partially over the coiled section to prevent fluid from escaping the lumen through the coiled section, the sleeve having a proximal end that is proximal to a proximal end of the coiled section and a distal end that is proximal to a distal end of the coiled section.

* * * * *

UNITED STATES PATENT AND TRADEMARK OFFICE
CERTIFICATE OF CORRECTION

PATENT NO.    : 6,500,147 B2
DATED         : December 31, 2002
INVENTOR(S)   : Isaac J. Kim et al.

It is certified that error appears in the above-identified patent and that said Letters Patent is hereby corrected as shown below:

Title page,
Item [75], please delete the following inventors:
"Samuel L. Omaleki, Morgan Hill, CA (US)
Celso J. Bagaoisan, Union City, CA (US)"

Signed and Sealed this

Twentieth Day of May, 2003

JAMES E. ROGAN
*Director of the United States Patent and Trademark Office*